(12) United States Patent
Schinazi

(10) Patent No.: US 10,376,633 B2
(45) Date of Patent: Aug. 13, 2019

(54) MICROFLOW RESTRICTOR ASSEMBLY AND METHODS OF MAKING THE SAME

(71) Applicant: L2R Enterprises, LLC, Las Vegas, NV (US)

(72) Inventor: Robert G. Schinazi, Oceanside, CA (US)

(73) Assignee: L2R Enterprises, LLC, Las Vegas, NV (US)

( * ) Notice: Subject to any disclaimer, the term of this patent is extended or adjusted under 35 U.S.C. 154(b) by 172 days.

(21) Appl. No.: 15/438,270

(22) Filed: Feb. 21, 2017

(65) Prior Publication Data

US 2017/0241583 A1 Aug. 24, 2017

Related U.S. Application Data

(60) Provisional application No. 62/298,168, filed on Feb. 22, 2016.

(51) Int. Cl.
*A61M 5/14* (2006.01)
*A61M 5/142* (2006.01)
(Continued)

(52) U.S. Cl.
CPC ............ *A61M 5/142* (2013.01); *A61M 5/141* (2013.01); *A61M 5/168* (2013.01); *A61M 39/10* (2013.01); *A61M 2207/00* (2013.01)

(58) Field of Classification Search
CPC .. F16L 55/02754; A61M 5/168; A61M 5/142; A61M 5/141; A61M 39/10; A61M 2207/00
See application file for complete search history.

(56) References Cited

U.S. PATENT DOCUMENTS

| 1,964,300 A | 6/1934 | Perry et al. |
| 2,021,079 A | 11/1935 | Mittendorf et al. |

(Continued)

FOREIGN PATENT DOCUMENTS

| EP | 0 271 785 A2 | 6/1988 |
| EP | 0 968 732 A2 | 1/2000 |

(Continued)

OTHER PUBLICATIONS

International Search Report & Written Opinion dated Jul. 20, 2017 in Int'l PCT Patent Appl. Serial No. PCT/US2017/018710.

*Primary Examiner* — Amber R Stiles
(74) *Attorney, Agent, or Firm* — Foley & Lardner LLP; Christopher C. Bolten; Albert K. Heng

(57) ABSTRACT

A medical fluid microflow assembly having an assembly fluid inlet and an assembly fluid outlet, and a mandrel having a curved exterior surface, the mandrel being positioned within an cavity of a housing so that the exterior surface of the mandrel is substantially parallel to an interior surface of the cavity, and at least one protrusion positioned helically around and extending from the interior surface of the cavity, each protrusion abutting the exterior surface of the mandrel to form a sealed fluid channel which has a channel inlet positioned proximate to the assembly fluid inlet and a channel outlet positioned proximate to the assembly fluid outlet, the exterior surface of the mandrel and the interior surface of the cavity having a minimal or neutral triboelectric value with respect to a fluid.

26 Claims, 21 Drawing Sheets

(51) Int. Cl.
*A61M 5/168* (2006.01)
*A61M 39/10* (2006.01)

(56) References Cited

U.S. PATENT DOCUMENTS

| | | | |
|---|---|---|---|
| 2,236,084 A | 3/1941 | Brown | |
| 2,341,394 A | 2/1944 | Sloan | |
| 2,511,733 A | 6/1950 | Morrison | |
| 2,771,878 A | 11/1956 | Folland et al. | |
| 2,857,927 A | 10/1958 | Pardee | |
| 2,878,836 A | 3/1959 | Binks | |
| 3,552,444 A | 1/1971 | Levesque | |
| 3,815,636 A | 6/1974 | Menzel | |
| 3,868,973 A | 3/1975 | Bierman et al. | |
| 3,998,427 A | 12/1976 | Bentley | |
| 4,022,384 A | 5/1977 | Hoyle et al. | |
| 4,150,696 A | 4/1979 | Meier et al. | |
| 4,200,119 A | 4/1980 | Cunningham | |
| 4,411,292 A | 10/1983 | Schiller | |
| 4,589,872 A | 5/1986 | Bellin et al. | |
| 4,639,019 A | 1/1987 | Mittleman | |
| 4,738,665 A | 4/1988 | Shepard | |
| 4,796,660 A | 1/1989 | Bron | |
| 5,032,264 A | 7/1991 | Geiger | |
| 5,156,680 A | 10/1992 | Orzechowski | |
| 5,549,583 A | 8/1996 | Sanford et al. | |
| 5,609,303 A | 3/1997 | Cohen | |
| 5,779,361 A | 7/1998 | Sugiura | |
| 6,497,685 B1 | 12/2002 | Dennehey et al. | |
| 6,550,956 B1 | 4/2003 | Utracki et al. | |
| 6,569,125 B2 | 5/2003 | Jepson et al. | |
| 6,569,128 B1 | 5/2003 | Christensen et al. | |
| 6,981,967 B2 | 1/2006 | Massengale et al. | |
| 7,325,572 B2 | 2/2008 | Schinazi et al. | |
| 7,364,571 B2 | 4/2008 | Schinazi et al. | |
| 7,608,061 B2 | 10/2009 | Schinazi et al. | |
| 2006/0196552 A1* | 9/2006 | Kriesel | A61M 5/141 137/487.5 |
| 2007/0131296 A1* | 6/2007 | Schinazi | A61M 5/141 138/43 |
| 2010/0204660 A1 | 8/2010 | McKinnon et al. | |
| 2011/0066108 A1* | 3/2011 | Geipel | A61M 5/141 604/151 |

FOREIGN PATENT DOCUMENTS

| | | |
|---|---|---|
| EP | 1 486 221 A1 | 12/2004 |
| WO | WO-2010/071795 A1 | 6/2010 |

* cited by examiner

MICROFLOW RESTRICTOR ASSEMBLY AND METHODS OF MAKING THE SAME

CROSS-REFERENCE TO RELATED APPLICATIONS

This application claims the benefit of priority of U.S. Provisional Application Ser. No. 62/298,168, filed Feb. 22, 2016, the entire contents of which are incorporated herein by reference.

FIELD OF THE INVENTION

The present invention relates generally to the field of flow restrictors, and more specifically to microflow restrictors useful in medical applications.

BACKGROUND OF THE INVENTION

Microflow restrictors are commonly used in the medical field in conjunction with infusion pump systems to regulate the flow of medicine and other fluids to a patient. Microflow restrictors are typically able to regulate fluid flow in the range of less than 500 milliliters per hour, but can regulate higher rates of flow if necessary. Typical pressures under which infusion pump systems operate are less than about 60 kPa.

Considerable difficulties with existing microflow restrictors are recognized in the prior art. Specifically, with regard to maintaining flow through the restrictor over time, prior art microflow restrictors are believed to be highly susceptible to seizing due to the presence of microparticulates and bubbles in the fluid. The small amount of fluid flowing through the restrictor and the minimal operating pressures of infusion pumps is believed to provide insufficient pressure to move or otherwise overcome the particulates or break the bubbles and permit fluid to continue to flow through the restrictor. To address this issue, select prior art microflow restrictors have been specifically designed to create multiple tortuous paths for fluid, such paths designed to break bubbles and permit particulates to be circumvented by the fluid.

However, prior art flow restrictors are expensive to manufacture due to the very small fluid pathways utilized. Some existing flow restrictors are manufactured using costly processing and post-processing steps. In addition, existing flow restrictors suffer from decreasing flow rates over time due to micro leaks within the flow restrictors.

SUMMARY OF THE INVENTION

The inventors have discovered, unexpectedly in view of the prior art, that triboelectric charges created by the fluid flowing through the microflow restrictor impact the flow of fluid through the restrictor over time. By managing the triboelectric effects of the fluid and microflow restrictor, the microflow restrictor is able to consistently function as intended over time. Additionally, the unique configuration of the fluid pathway in the present invention permits better management of triboelectric effects while at the same time simplifying manufacturing processes and reducing manufacturing costs. Hence, the present invention enables management of very small amounts of fluid flow over time without significant interference from triboelectric effects in a microflow restrictor configuration that permits manufacturing in a more cost-effective manner.

The present invention is directed to a medical fluid microflow assembly which includes an assembly fluid inlet and an assembly fluid outlet. A mandrel having an exterior surface is positioned within a cavity of a housing so that at least a portion of the exterior surface of the mandrel is substantially parallel to at least a portion of an interior surface of the cavity. At least one protrusion extends from either the interior surface of the cavity or the exterior surface of the mandrel, each protrusion abutting either the exterior surface of the mandrel or the interior surface of the cavity to form a sealed fluid channel. The sealed fluid channel may include a channel inlet positioned proximate to the assembly fluid inlet and a channel outlet positioned proximate to the assembly fluid outlet.

The sealed fluid channel has a length and an average width and, in certain embodiments, the length of the channel may be greater than ten times the average width of the sealed fluid channel. The average width of the sealed fluid channel may be at least 50 microns and in some embodiments maybe wider than 50 microns. The sealed fluid channel may have a constant width along at least a portion of the length of the sealed fluid channel, or may have a width that varies along at least a portion of the length of the channel. In certain embodiments, the width of the sealed fluid channel may increase along at least a portion of the length of the channel so that the sealed fluid channel is widest proximate to the channel outlet.

The exterior surface of the mandrel may be variously shaped and may have a conical shape so that the sealed fluid channel may extend about the exterior surface of the mandrel in a helical pattern.

In particular embodiments, a portion of the exterior surface of the mandrel may be planar. At least a portion of the interior surface of cavity may be configured to be substantially parallel to the planar portion of the exterior surface of the mandrel. In configurations where at least two portions of the exterior surface of the mandrel are planar, both portions being substantially parallel to at least a portion of the interior surface of the cavity, a protrusion may be positioned on each planar surface of either the mandrel or the cavity so that at least two sealed fluid channels are formed.

The protrusion may extend from either the planar portion of the exterior surface of the mandrel or the interior surface of the cavity. In some embodiments, protrusions may extend from the exterior surface of the mandrel and the interior surface of the cavity.

The sealed fluid channel has an average height which is the average distance between the exterior surface of the mandrel and the interior surface of the cavity of the housing in some embodiments. The sealed fluid channel also has an average width, and in some embodiments the average width of the sealed fluid channel is at least the same as, e.g., at least 3 times, at least 5 times, or at least 10 times, the average height of the sealed fluid channel. In certain configurations, the average height of the sealed fluid channel may be equal to or greater than about five (5) microns and less than about five hundred (500) microns. At least one of the surfaces which form the sealed fluid channel may have an average surface roughness that is less than about ten percent (10%), e.g., less than about five percent (5%), of the average height of the sealed fluid channel, and ideally, as smooth as possible.

The protrusion may include a first surface and a second surface, the first and second surfaces forming an apex which contacts either the exterior surface of the mandrel or the interior surface of the cavity to form the sealed fluid channel. In some configurations the apex may be formed as a radius, which may in certain configurations be greater than or equal to 0.001 microns.

The sealed fluid channel may be at least partially formed from a material that exhibits a substantially neutral triboelectric charge when in contact with a saline or glucose solution. To achieve this, the sealed fluid channel may be at least partially formed from polycarbonate. Portions of the sealed fluid channel may also be formed from polysulfone, acrylic, PVC, Nylon, Polyethylene, Polypropylene polymers, or combinations of these materials with polycarbonate.

The medical fluid microflow assembly may be configured so that the sealed fluid channel permits fluid to flow through the assembly fluid outlet at a flow rate greater than about 0.01 ml per hour, and in some configurations at a flow rate of less than about 500 ml per hour.

In accordance with another aspect of the present invention, a method for manufacturing a medical fluid microflow assembly is provided. The method may include forming a medical fluid microflow assembly housing comprising a cavity, and forming a mandrel comprising an exterior surface. In addition, prior to hardening at least one of the material of the medical fluid microflow assembly housing or the mandrel, the mandrel may be positioned within the cavity of the medical fluid microflow assembly housing such that at least one partially-hardened protrusion extending from either an interior surface of the cavity or the exterior surface of the mandrel abuts either the exterior surface of the mandrel or the interior surface of the cavity to form a sealed fluid channel. The partially-hardened material has a greater capacity to deform and thereby compensate for geometric and manufacturing variations, forming a more perfect seal between microflow assembly housing and mandrel, and decreasing propensity for microleaks. After positioning the mandrel within the cavity of the medical fluid microflow assembly housing, the mandrel and/or the medical fluid microflow assembly housing are hardened either through time, temperature, chemical, or other means. In one embodiment, the medical fluid microflow assembly is assembled when all components are fully hardened except for the medical fluid microflow assembly housing which is partially-hardened during assembly. In another embodiment, only the mandrel is partially hardened during assembly of the medical fluid microflow assembly.

In another embodiment, the method includes achieving a desired flow rate through the microflow assembly. For example, the method may include loading a medical fluid microflow assembly housing having a cavity into a fixture, and applying a curing adhesive on a portion of the interior surface of the cavity of the housing between the interior surface of the cavity and the post. The method further may include monitoring an airflow rate of a pressurized gas or a pressure differential between the inlet and outlet, e.g. a vacuum at the outlet, passing the pressurized gas through the sealed fluid channel from the channel inlet to the channel outlet, and adjusting the pressing of the post against the mandrel based on the monitored airflow rate. The curing adhesive may then be cured when the measured airflow rate reaches a target airflow rate.

DETAILED DESCRIPTION

Figure 1A:
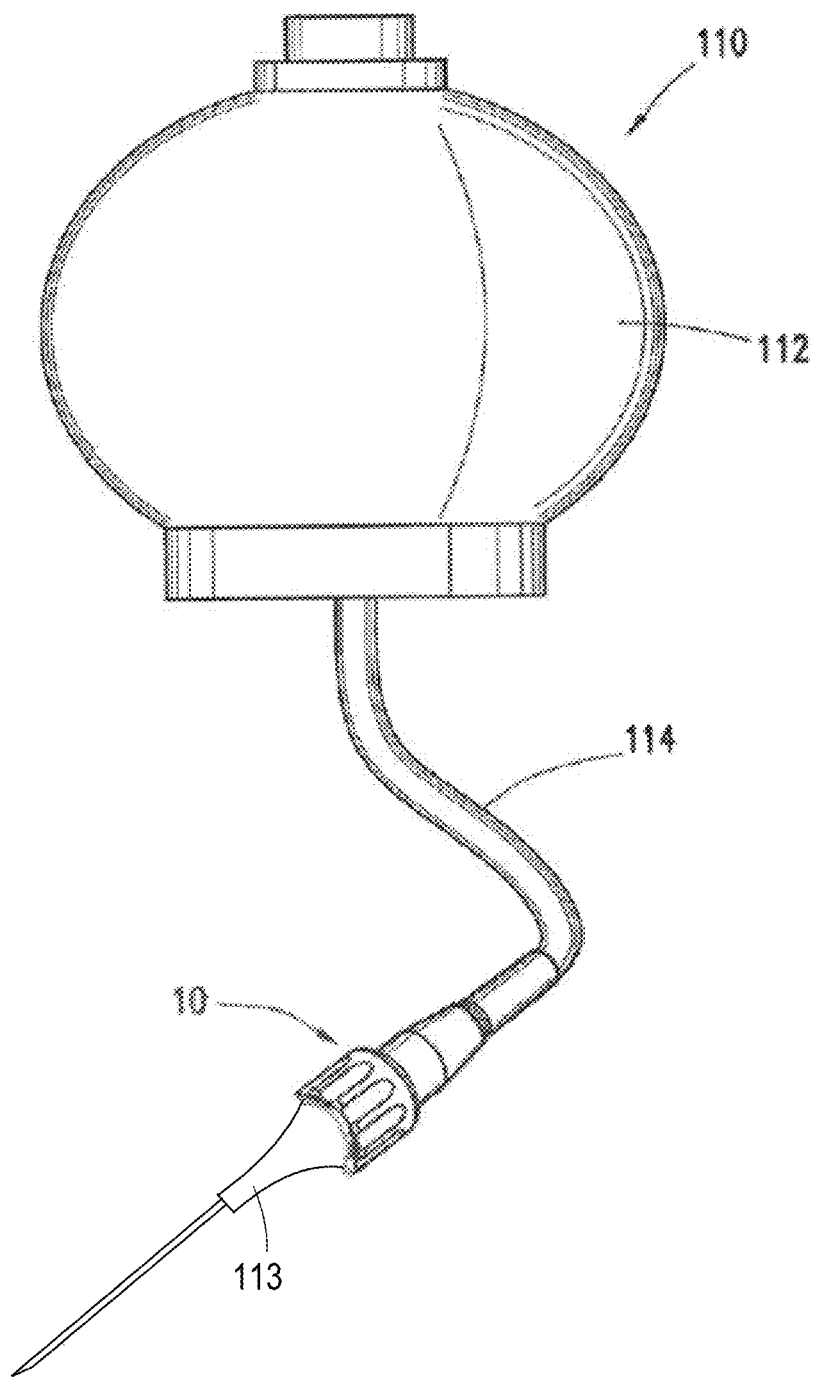
FIG. 1A is a perspective view of an infusion pump system utilizing an embodiment of a microflow assembly according to an aspect of the present invention.

The invention will now be described with reference to one or more embodiments which are illustrated in the drawings. It is to be understood that the detailed description is provided by way of explanation of the invention and is not meant as a limitation of the invention. For instance, features illustrated and described as part of one embodiment may be used on another embodiment to yield a still further embodiment.

It is intended that the present invention include these and other modifications and variations to the embodiments described herein.

FIG. 1A illustrates ambulatory infusion pump system 110 for delivery of fluids to a patient. Ambulatory infusion pump system 110 typically includes reservoir 112, a reservoir support, and tubing 114 through which fluid from reservoir 112 flows. Reservoir 112 also may function as a pump and is typically a rubber or elastomeric bladder which is designed to exert a constant pressure on the contents of the pump during the infusion process. Typical pressures in the ambulatory infusion pump system can range of from about 20 kPa to about 60 kPa.

Figure 1B:
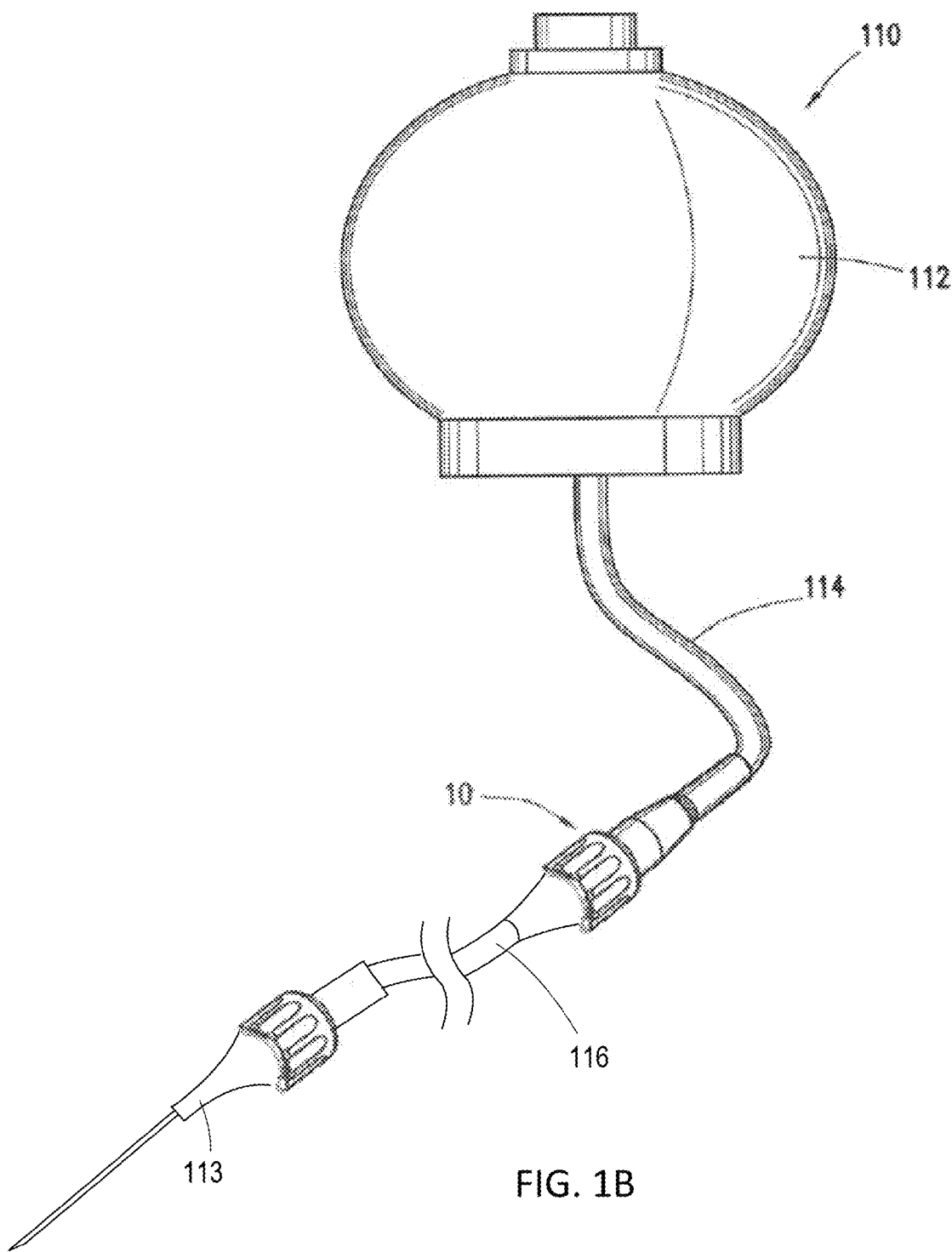
FIG. 1B is another perspective view of an infusion pump system utilizing an embodiment of a microflow assembly according to another aspect of the present invention.

As shown in FIGS. 1A and 1B, a fluid inlet of microflow restrictor 10 may be connected to medical tubing 114 to receive fluid from reservoir 112. Fluid passes through microflow restrictor 10 and exits through a fluid outlet of microflow restrictor 10 into needle assembly 113 to flow to the patient as shown in FIG. 1A or into medical tubing 116 to flow to the patient as shown in FIG. 1B.

Microflow assembly 10 may be configured to engage and retain various articles at its assembly fluid inlet 28 and assembly fluid outlet 26 (both shown in FIG. 3A), such as medical tubing, luer lock connectors, as well as any other of a multitude of mechanisms available to form fluid pathways.

Microflow restrictor assembly 10 may be utilized to restrict the flow of fluids to the patient. Microflow restrictor assembly 10 may be connected to reservoir 112 via medical tubing 114 and may be connected to a patient using a variety of mechanisms. For example and as shown in FIG. 1A, microflow restrictor assembly 10 may be connected at one end to medical tubing 114 and at its other end to needle assembly 113 configured to engage an established intravenous site of a patient. In other configurations and as shown in FIG. 1B, microflow restrictor assembly 10 may be connected to medical tubing 116 which may have needle assembly 113 connected to its other end. Optionally, multiple microflow restrictor assembles may be used in a fluid path between reservoir 112 and the patient. For example, in FIG. 1B, fluid flows from reservoir 112 into medical tubing 114, through microflow restrictor assembly 10 into medical tubing 116, through a second microflow restrictor assembly, into needle assembly 113 and to the patient. Other articles may be utilized in place of needle assembly 113, including catheters, luer lock fittings, or other specialized fittings.

Figure 3A:
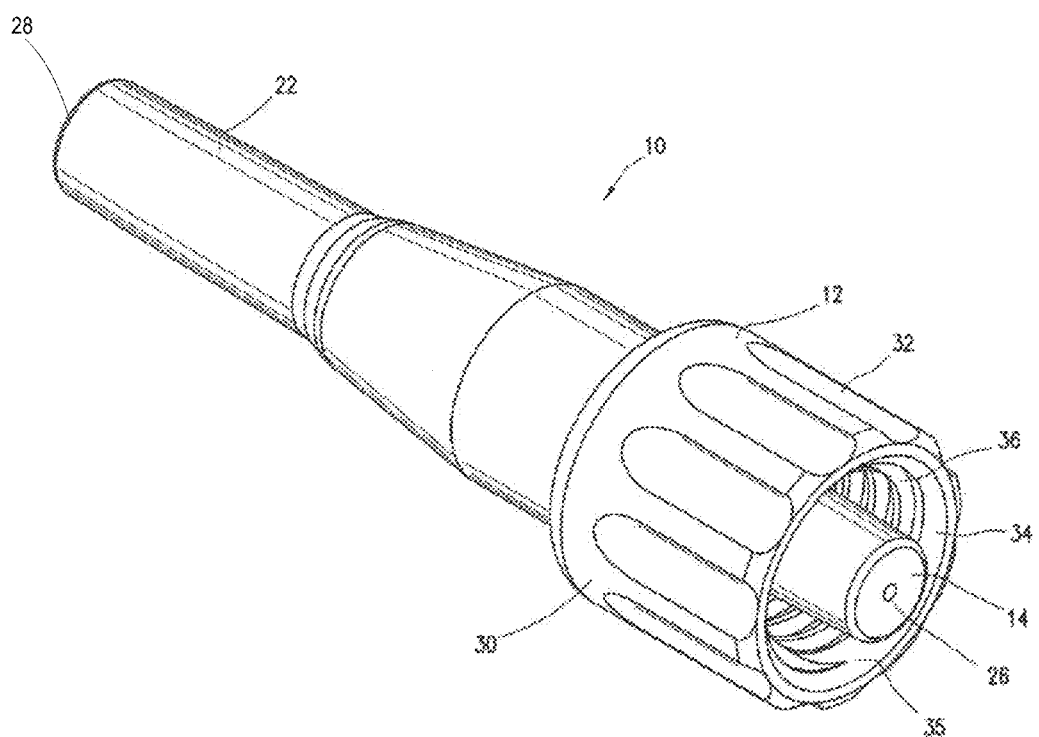
FIG. 3A is a perspective view of an embodiment of a microflow assembly according to the present invention.
Figure 3B:
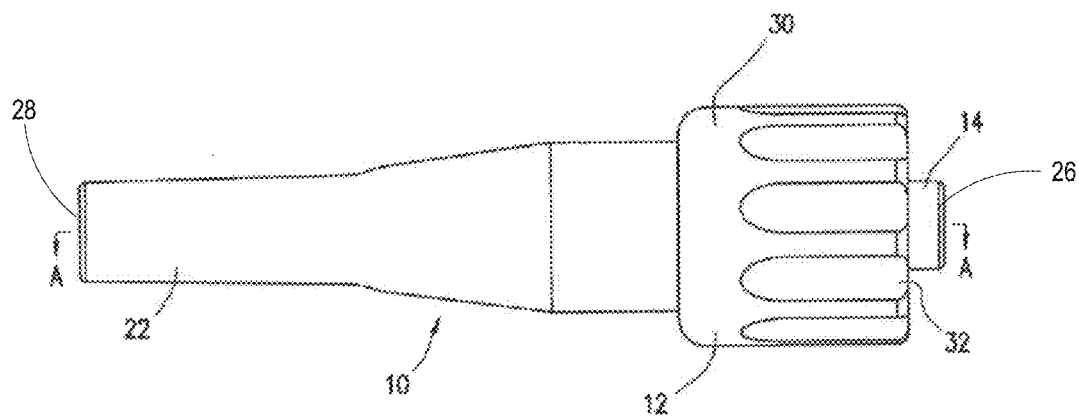
FIG. 3B is a side view of the embodiment of the microflow assembly depicted in FIG. 3A.
Figure 4A:
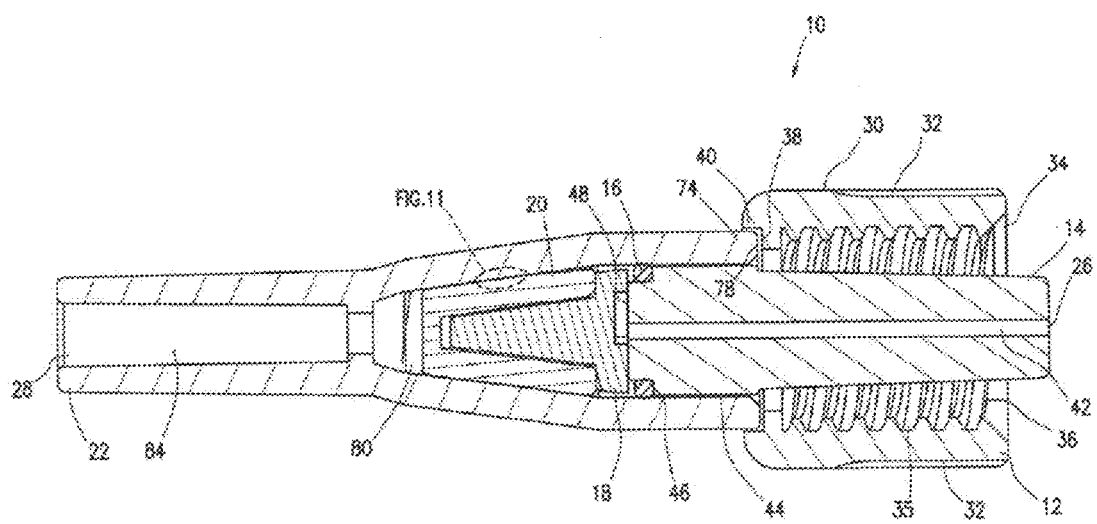
FIG. 4A is a cross-sectional view of the microflow assembly depicted in FIG. 3B, taken along line A-A.
Figure 4B:
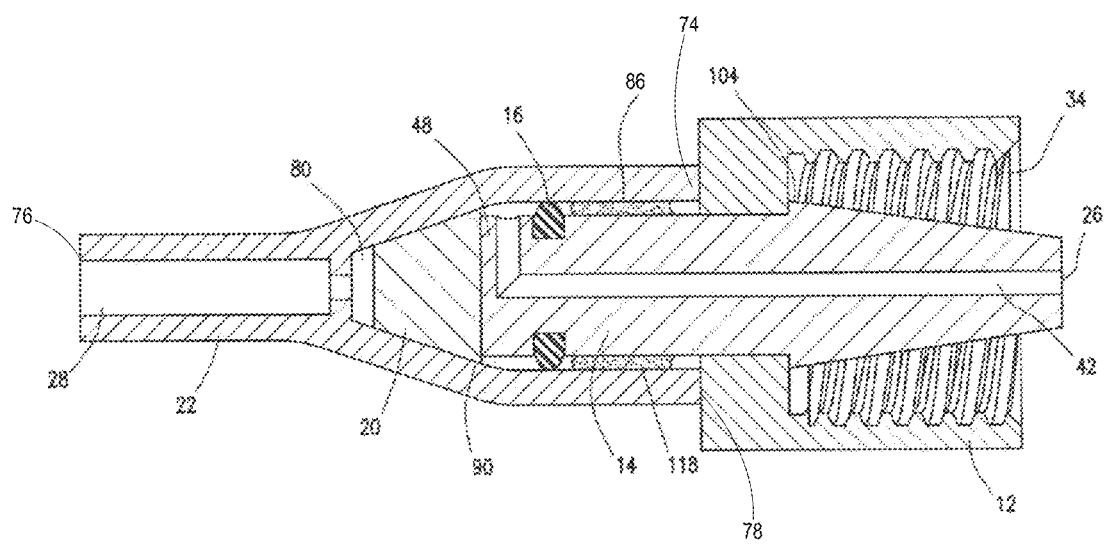
FIG. 4B is a cross-sectional view of an embodiment of the microflow assembly.

Referring to FIGS. 2A-4B, a medical fluid microflow assembly is shown therein. Microflow assembly 10 includes assembly fluid inlet 28 and assembly fluid outlet 26, which are fluidly connected so that fluid entering assembly fluid inlet 28 passes through microflow assembly 10 and exits microflow assembly 10 through assembly fluid outlet 26. Assembly fluid inlet 28 may, in some embodiments and as shown in FIGS. 4A and 4B, be positioned in housing 22. Assembly fluid outlet 26, in some embodiments and as shown in FIGS. 4A and 4B, may be positioned in post 14.

Figure 2A:
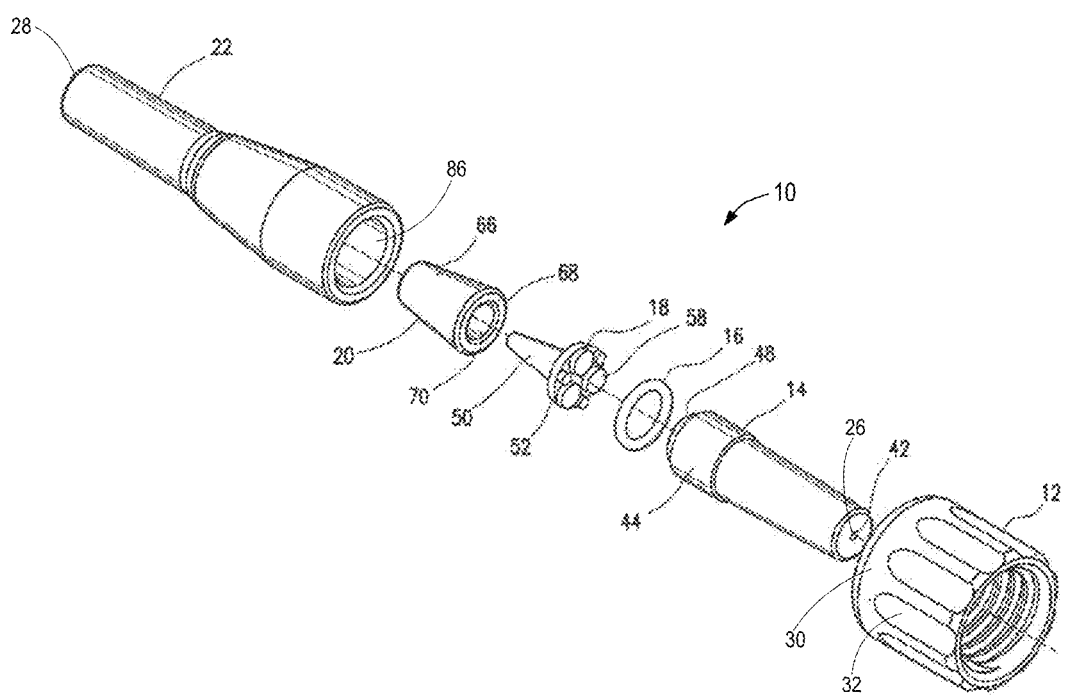
FIG. 2A is a perspective exploded view of the microflow assembly of FIG. 1A.

FIG. 2A is an exploded view of an embodiment of microflow assembly 10 which includes housing 22, mandrel 20, dowel 18, seal 16, post 14, and connector 12. Other embodiments of microflow assembly 10 may be configured so that selected elements, such as mandrel 20 and dowel 18 are formed as a single piece. For example, housing 22 and connector 12 may be formed as a single piece, which may also include seal 16. Post 14, seal 16, dowel 18, and mandrel 20 may also be formed as a single piece. In certain embodiments, selected pieces may be omitted for ease of manufacturing.

As seen in FIG. 2A, mandrel 20 is positioned within housing 22 and may include cavity 70, end 68, and exterior surface 66. Dowel 18 may be useful in embodiments where mandrel 20 is formed with central cavity 70. Body 50 of dowel 18 may be positioned within cavity 70 of mandrel 20 and may be useful to provide support to mandrel 20. Body 50 of dowel 18 may occupy only a portion of central cavity 70.

Post 14 is configured to move dowel 18 and mandrel 20 into cavity 80 within housing 22. In select embodiments, post 14 and dowel 18 may be formed as a single element. Depending on the suitability for specific manufacturing processes, post 14, seal 16, dowel 18, and connector 12 may be formed as one or multiple elements. For example, post 14 and dowel 18 may be formed as a single element. In other embodiments, post 14, dowel 18, and connector 12 may be formed as a single element. Post 14, mandrel 20, and dowel 18 may be formed as a single element or may be joined via adhesive, ultrasonic welding, screws or snap-together features.

Seal 16 may be formed as a part of post 14 or may be separately formed and positioned between post 14 and interior surface 86 of housing 22. For example, seal 16 may be positioned within detent 46 of post 14 such that seal 16 is in contact with an exterior surface of post 14 and interior surface 86 of housing 22. Seal 16 functions to ensure that fluid is transmitted only through passage 42 and prevents fluid bypassing the restricted flow channel which meters the appropriate flow of fluid through microflow assembly 10. Seal 16 also helps prevent adhesive used to join post 14 to interior surface 86 of housing 22 from interfering with the flow of fluid through microflow restrictor assembly 10. Seal 16 may be formed from any of a variety of materials including silicone, rubber or other suitable materials. In certain embodiments, post 14 and seal 16 may be formed as a single element, and seal 16 may be co-molded with post 14, mandrel 20, dowel 18, or housing 22. Post 14, seal 16, and connector 12 may also be formed as a single element.

Figure 2B:
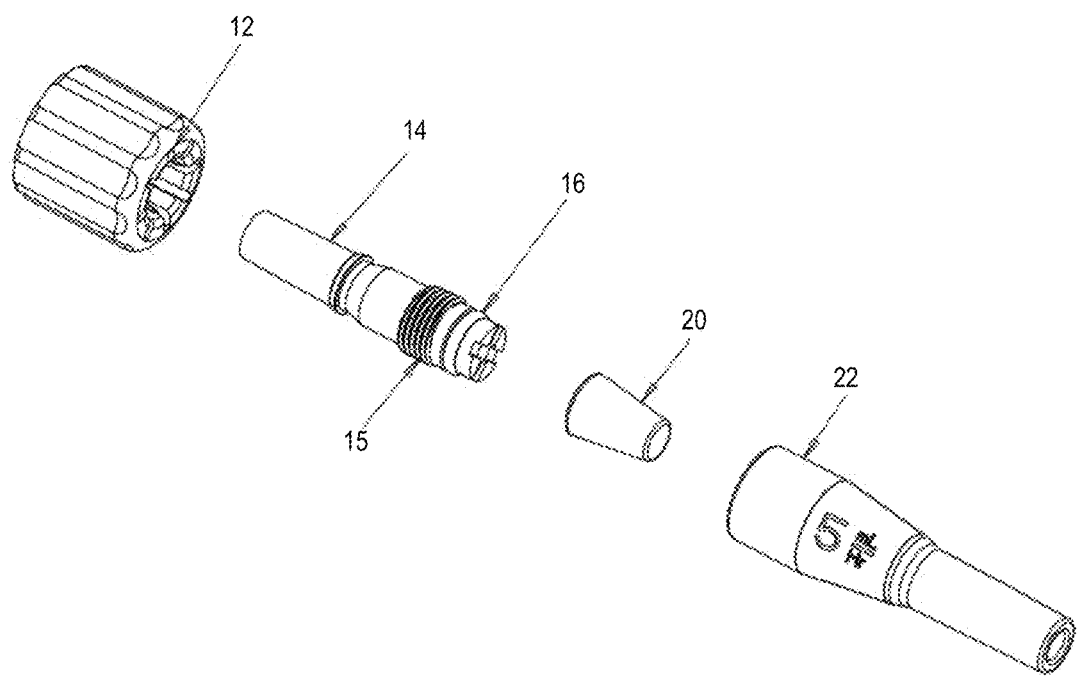
FIG. 2B is a perspective exploded view of another embodiment of the microflow assembly.

FIG. 2B is an exploded view of another embodiment of microflow assembly which includes housing 22, mandrel 20, seal 16, post 14, and connector 12. As seen in FIG. 2B, post 14 may include threaded feature 15. In addition, housing 22 may include a spiral groove and post 14 may include a spiked portion. Seal 16 may be over cast molded.

FIG. 3A shows an embodiment of microflow assembly 10 as assembled and depicts assembly fluid outlet 26 which is positioned in post 14. Assembly fluid inlet 28, shown in FIG. 4, is positioned in housing 22. FIG. 3B illustrates a side view of the assembled microflow assembly 10 of FIG. 3A.

As shown in FIGS. 3A and 3B, exterior surface 30 of connector 12 may include features to enhance its ease of use, such as indentations 32. Indentations 32, or other gripping features may be variously formed such as, for example, ribs, knurling or simply a rough surface texture.

Connector 12 includes opening 34 which may extend through connector 12. Threads 36 may be formed into interior surface 35 of opening 34, to permit a source of fluid to be releasably engaged to microflow assembly 10. Luer lock fittings and snap-fit connections are particularly well-suited for use in conjunction with connector 12.

As shown in FIGS. 4A and 4B, housing 22 further includes end 78 which may be positioned adjacent to connector 12. Connector 12, in selected embodiments, may include recessed surface 38 and shoulder 40 which are configured to engage housing 22. As shown in FIG. 4B, post 14 and connector 12 may be designed so that connector 12 snaps onto, or is otherwise mechanically connected to, post 14.

End 78 of housing 22, which is adjacent to outlet portion 74, abuts recessed surface 38 of connector 12. Shoulder 40 of connector 12 may extend around at least a portion of outlet portion 74 of housing 22. In certain embodiments, housing 22 and connector 12 may be press-fit together or may be secured by adhesive or other joining processes such as ultrasonic welding, retention features, or fasteners. As depicted in the microflow assembly of FIG. 4B, housing 22 may simply abut connector 12 and be secured in position by other elements of microflow assembly 10. In particular embodiments, housing 22 and connector 12 may be integrally formed as a single element.

The embodiment of the microflow assembly depicted in FIG. 4B shows mandrel 20 is positioned within cavity 80 of housing 22, mandrel 20 having no cavity and being in contact with post 14. Mandrel 20 and post 14 may be formed as a single element or may be joined by adhesive, retention mechanisms, ultrasonic welding and the like.

Figure 5:
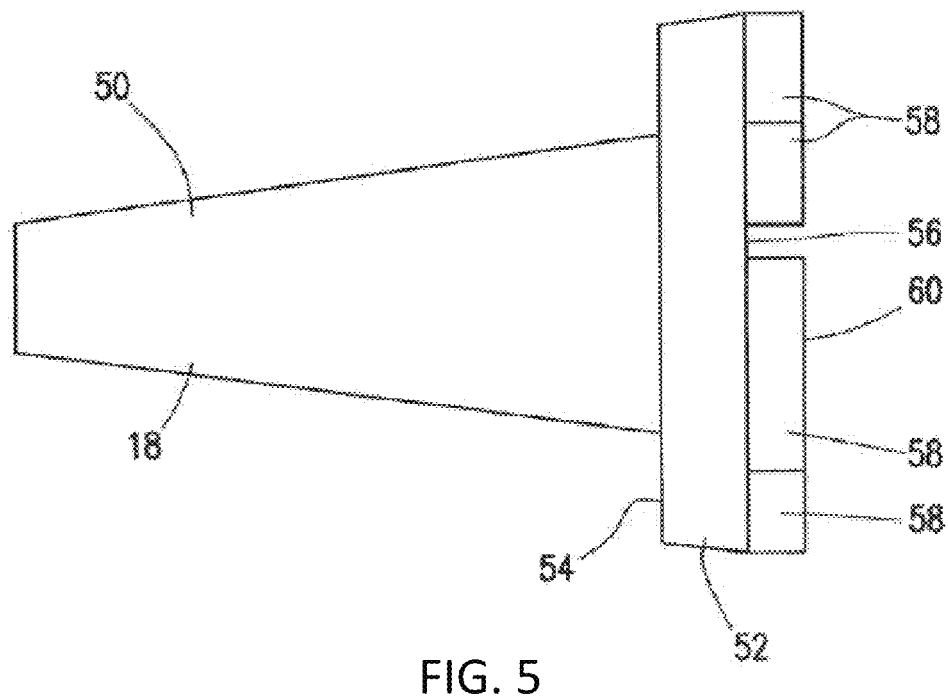
FIG. 5 is a side view of an embodiment of a fluid dowel useful in the present invention.
Figure 6:
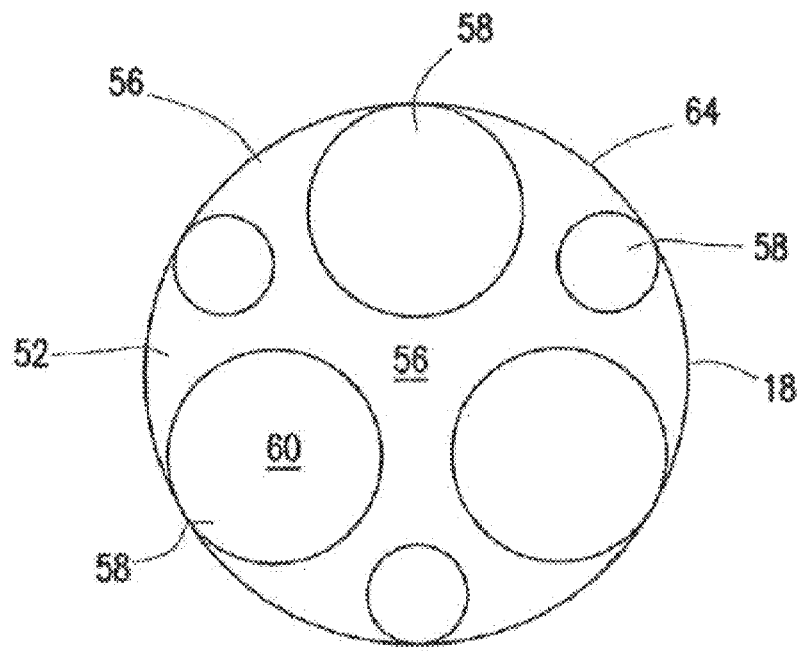
FIG. 6 is an end view of the fluid dowel depicted in FIG. 5.
Figure 7:
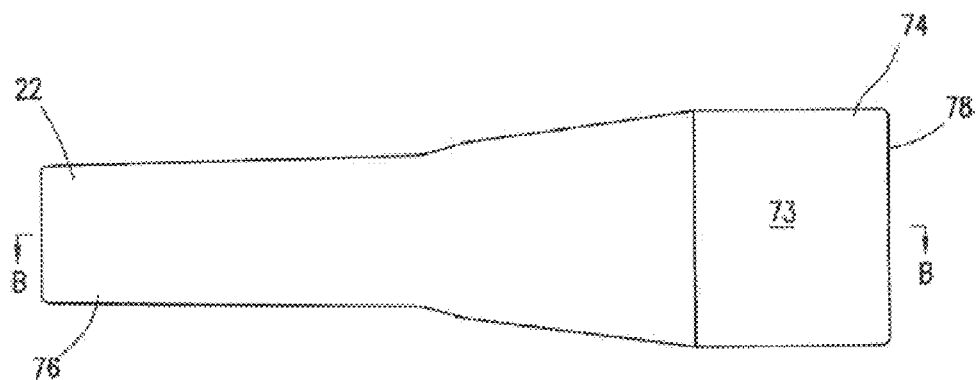
FIG. 7 is a side view of an embodiment of a housing useful in the present invention.

As shown in FIGS. 5 and 6, dowel 18 may further include disk 52 having circumference 64, lower surface 54 which may be positioned adjacent to end 68 of mandrel 20. Disk 52 may include upper surface 56 upon which may be positioned at least one boss 58 and, in some embodiments, a plurality of bosses 58. Upper surfaces 60 of the each boss 58 may contact post 14.

FIGS. 4A-4C and 7-10 depict housing 22 useful in the present invention. Housing 22 includes outlet portion 74 and inlet portion 76. In the embodiment depicted in FIGS. 7 and 8, assembly fluid inlet 28 is positioned proximate to inlet portion 76 of housing 22. Exterior surface 73 of housing 22 may be variously formed to suit the particular needs of the user. The exterior of the housing may be configured to enable a user to easily and securely grasp housing 22. Information regarding the characteristics of microflow assembly 10 may be imprinted on housing 22.

Figure 8:
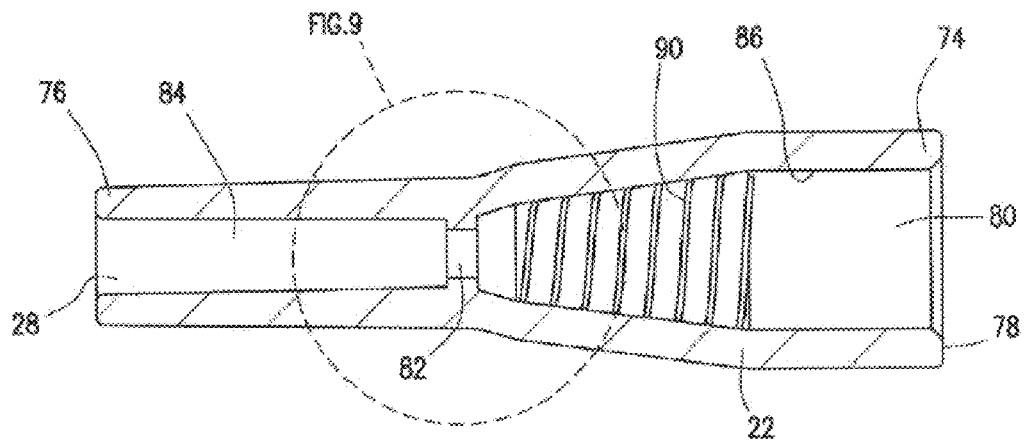
FIG. 8 is a cross-sectional view of the housing depicted in FIG. 7, taken along line B-B.

As shown in FIG. 8, housing 22 includes interior surface 86 which forms cavity 80. Cavity 80 may have areas such as inlet portion 84 and transition portion 82. Interior surface 86 of housing 22 may be variously shaped, and may have some portions which are planar, curved, conical, or other shapes.

As shown in FIG. 4A, in select embodiments, assembly fluid inlet 28 may be positioned adjacent to cavity 80, and cavity 80 may have inlet portion 84. Fluid enters microflow assembly 10 through assembly fluid inlet 28 in housing 22.

Figure 11:
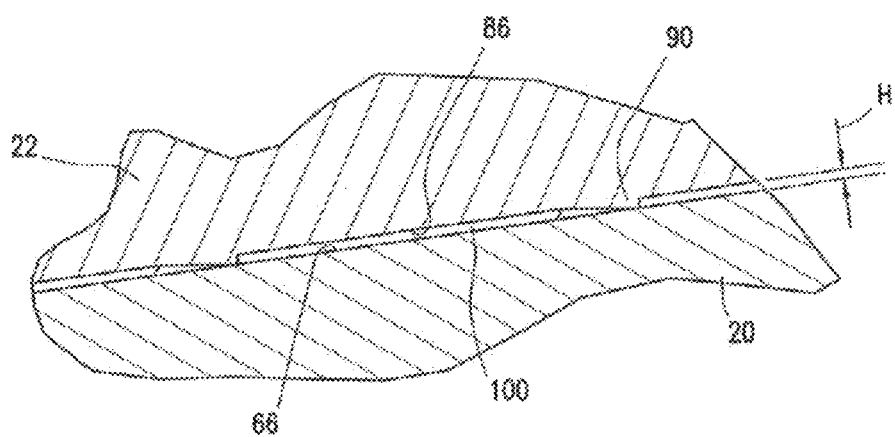
FIG. 11 is an enlarged view of an encircled portion of the microflow assembly depicted in FIG. 4A.

As best shown in FIG. 11, exterior surface 66 of mandrel 20 is positioned proximate to interior surface 86 of cavity 80 of housing 22.

Post 14, shown in FIGS. 2A and 4A-4C, has inlet end 48. Passage 42 in post 14 extends from inlet end 48 to assembly fluid outlet 26. Inlet end 48 of post 14 is positioned in contact with bosses 58 of dowel 18 or mandrel 20. As seen in FIGS. 2A and 4A, post 14 may also include collar 44 extending outwardly from and encircling at least a portion of post 14 proximate to inlet end 48. Upon assembly of post 14 into housing 22, collar 44 may be configured so that a gap is formed between either collar 44 and interior surface 86 of cavity 80 or the exterior surface of post 14 and interior surface 86 of cavity 80. Adhesive may be used to secure post 14 to housing 22 and, in select embodiments, to mandrel 20. A wicking-type adhesive may be used to fill the gap and secure the components together. Such an adhesive may be applied after post 14 has been positioned within housing 22.

The gap between post 14 and housing 22 may range from about 0.01 mm to about 1.25 mm, and may be about 0.075 mm in selected embodiments.

Figure 4C:
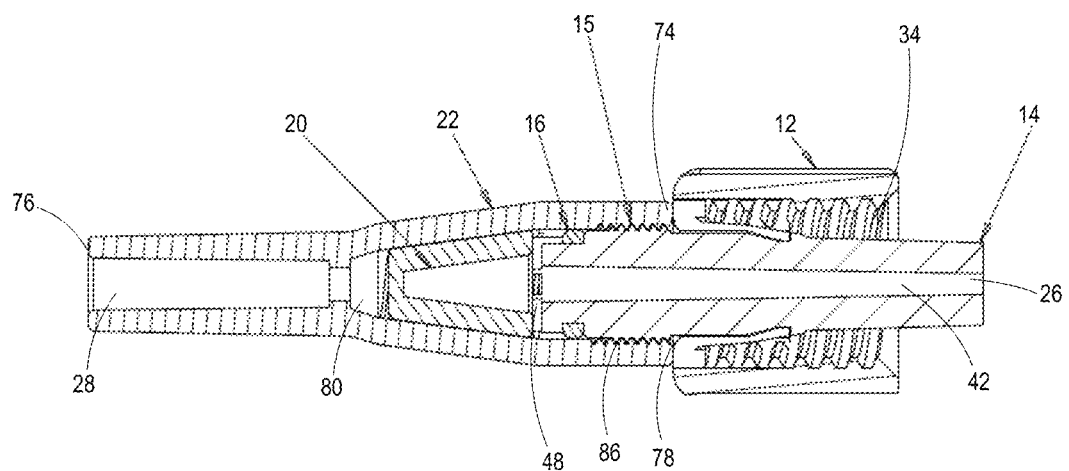
FIG. 4C is a cross-sectional view of the assembled microflow assembly depicted in FIG. 2B.

As seen in FIG. 4C, which is a cross-sectional view of the microflow assembly depicted in FIG. 2B in an assembled configuration, post 14 may include threaded feature 15. Threaded feature 15 may engage with at least a portion of interior surface 86 of housing 22.

Referring to FIGS. 8-13B, at least one protrusion 90 is positioned on either interior surface 86 of cavity 80 of housing 22, or on exterior surface 66 of mandrel 20. FIG. 8 shows protrusion 90 positioned on interior surface 86, in the area in which mandrel 20 will be positioned. Protrusion 90 may extend along a substantial length of housing 22, and in some embodiments may extend beyond the length of mandrel 20. This permits flexibility in the process by which microflow assembly 10 is constructed by enabling a wider variation in the positioning of mandrel 20 within housing 22.

Figure 9:
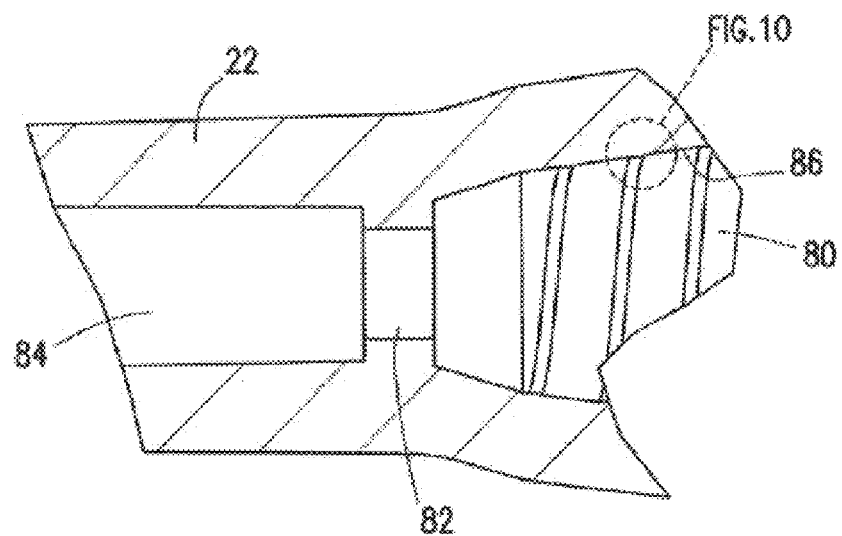
FIG. 9 is an enlarged view of an encircled portion of the housing depicted in FIG. 8.
Figure 10:
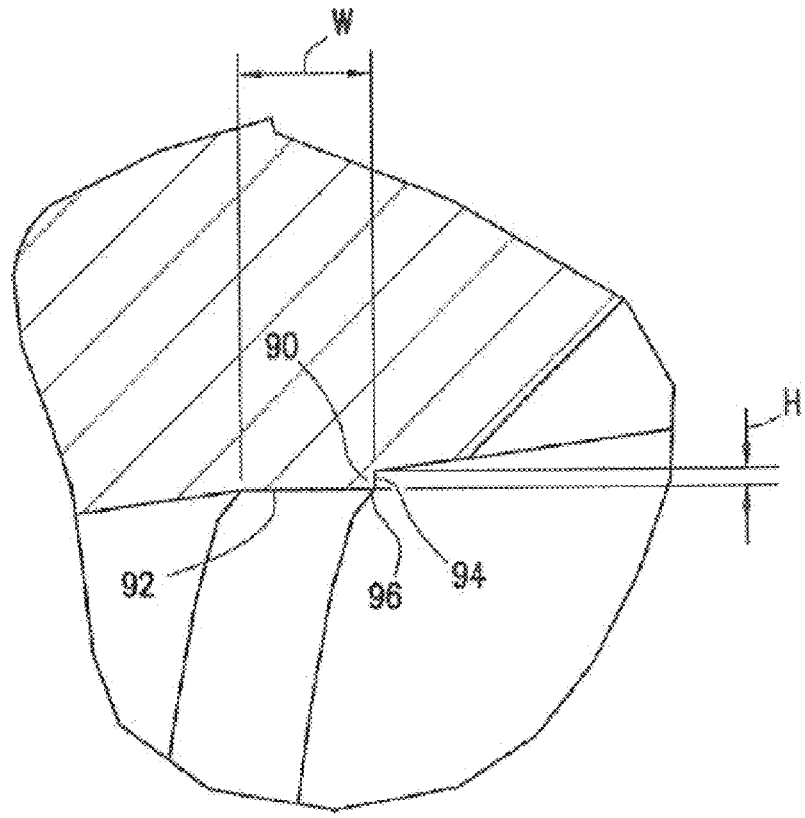
FIG. 10 is an enlarged view of an encircled portion of the housing depicted in FIG. 9.

FIGS. 9 and 10 show an embodiment of protrusion 90 in greater detail. Protrusion 90 may be formed as a ramp having a width W and a height H at its highest end. Protrusion 90 may include first surface 92 and second surface 94, first and second surfaces 92, 94 forming apex 96 as shown in FIG. 10. Protrusion 90 may extend along interior surface 86 or exterior surface 66 of mandrel 20 for a length sufficient so that it forms at least two complete wraps about the circumference of interior surface 86.

FIG. 11 shows protrusion 90 which abuts exterior surface 66 of mandrel 20. As seen therein, sealed fluid channel 100 is formed between interior surface 86, exterior surface 66, and protrusion 90. In the embodiment shown in FIGS. 8-11, sealed fluid channel 100 forms a helical path for fluid through microflow restrictor assembly 10.

Figure 12A:
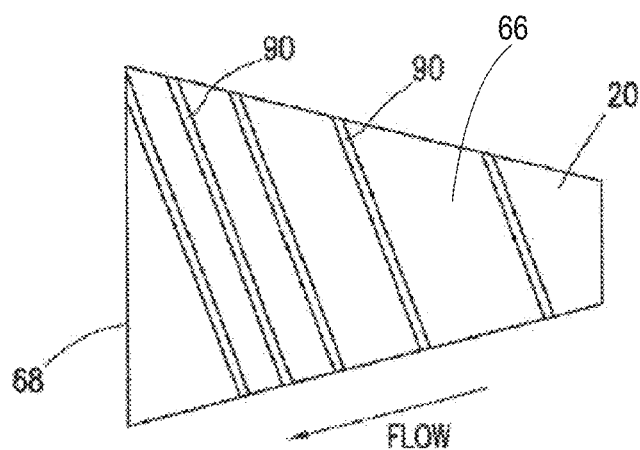
FIG. 12A is a side view of an embodiment of the mandrel.
Figure 12B:
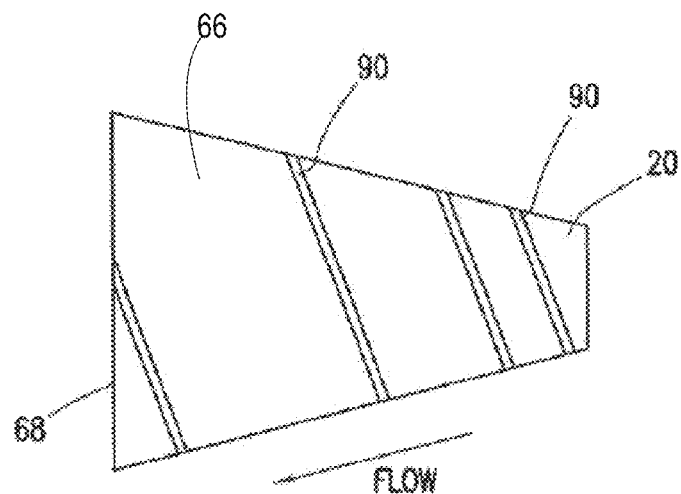
FIG. 12B is a side view of another embodiment of the mandrel.
Figure 12C:
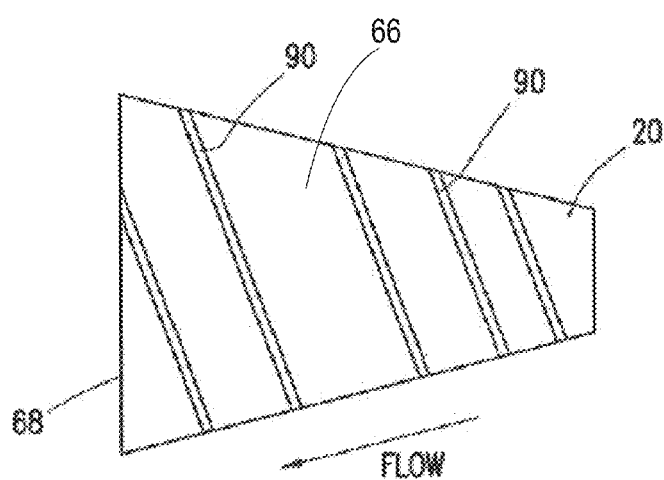
FIG. 12C is a side view of yet another embodiment of the mandrel.

In particular embodiments, protrusion 90 has a length that extends in a substantially continuous helix on at least a portion of interior surface 86 or exterior surface 66. Protrusion 90 may be positioned on such surface in different manners. For example, the distance between the successive wraps of protrusion 90, or pitch of protrusion 90, may increase or decrease with respect to the direction of flow of fluid through the assembly. The pitch of protrusion 90 may also be uniform or non-uniform along the length of the surface. For example and as illustrated in FIG. 12A, protrusion 90 is positioned on exterior surface 66 of mandrel 20, and the pitch of protrusion 90 decreases in the direction of flow. The pitch of protrusion 90 shown in FIG. 12B increases with respect to the direction of fluid flow. FIG. 12C illustrates a non-uniform positioning of protrusion 90 on surface 66. FIGS. 12A-12C are illustrative only as protrusion 90 may form many more wraps about surface 66.

Many configurations of protrusion 90 are suitable for use in the present invention, including protrusions having cross-sectional shapes which are triangular, elliptical, orthogonal, or circular. However, it is desirable to select a cross-sectional area at apex 96 (shown in FIG. 10) which will focus the compressive load during assembly of mandrel 20 and housing 22, and permit controlled deformation of the small total area at apex 96. This permits local stresses at apex 96 to exceed the plastic limit of the material from which protrusion 90 is formed.

The local deformation of protrusion 90 is preferably configured to avoid the creation of hoop stresses in housing 22 sufficient to cause cracking. The materials selected for protrusion 90, housing 22, and mandrel 20 will impact the robustness of microflow assembly 10 to cracking. Additionally, the angle of exterior surface 66 of mandrel 20 will impact the resistance of housing 22 to cracking. In some embodiments, an angle of seven degrees (fourteen degree included angle) permits mandrel 20 to be self-locking while not producing excessive hoop stresses. Angles of between five and nine degrees (ten and eighteen degree included angles) are also suitable for use in the present invention.

As described above, sealed fluid pathway 100 of the present invention is formed by interior surface 86 of housing 22 and exterior surface 66 of mandrel 20. The particular configuration of mandrel 20 and housing 22 may be variously structured to achieve sealed fluid pathway 100. In some embodiments, interior surface 86 of housing 22 provides a tapered conical recess into which mandrel 20 is positioned. Exterior surface 66 of mandrel 20 may be formed as a corresponding tapered conical surface from which protrusions 90 extend.

As shown in FIGS. 13A-13D, exterior surface 66 of mandrel 20 may at least partially include a planar surface of a wedge. These types of mandrels 20 will be suitable for use in housings 22 having at least a portion of their interior surface 86 formed as an angled planar surface.

Figure 13A:
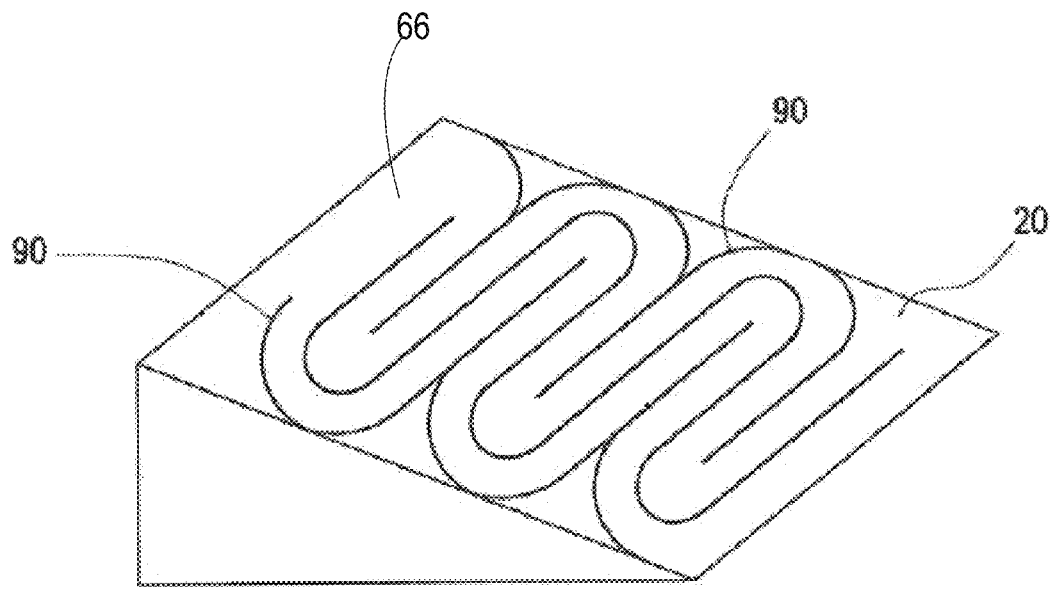
FIG. 13A is a perspective view of still another embodiment of the mandrel.
Figure 13B:
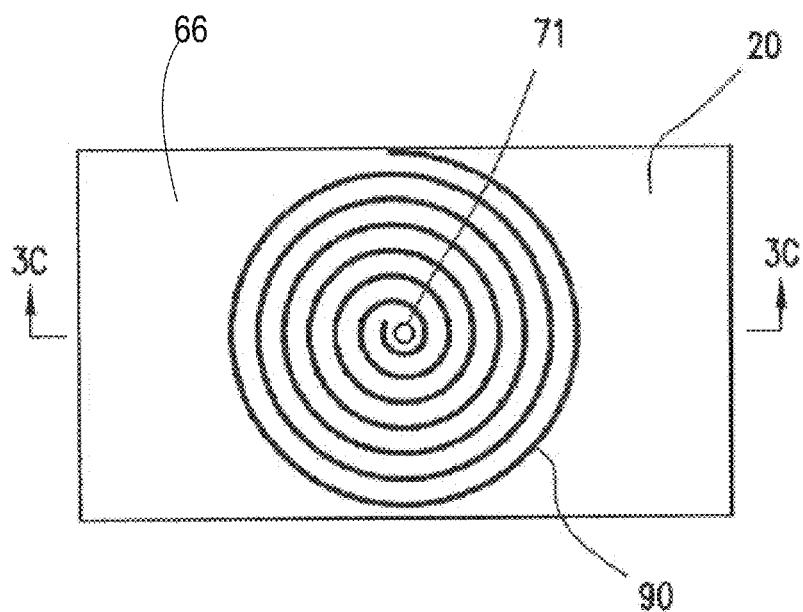
FIG. 13B is a top view of an alternate embodiment of the mandrel.
Figure 13C:
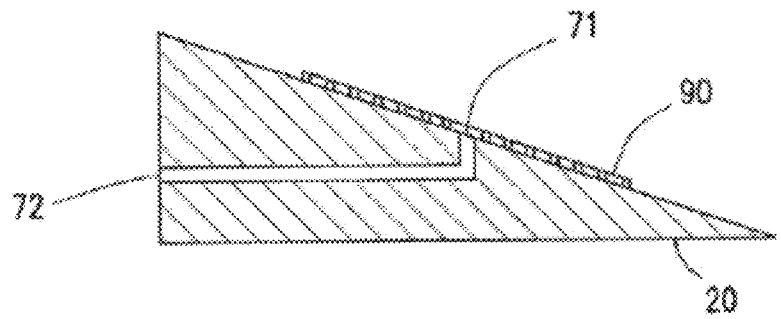
FIG. 13C is a cross-sectional view of the mandrel depicted in FIG. 13B.

FIG. 13A shows mandrel 20 formed as a wedge upon which protrusion 90 is positioned. Interior surface 86 of housing 22 should be shaped so that at least a portion of interior surface 86 is substantially parallel to and spaced apart from exterior surface 66 of mandrel 20 when mandrel 20 is inserted into housing 22.

As shown in FIG. 13A, protrusion 90 is positioned on mandrel 20 so that two sealed fluid channels 100 are created when wedge-shaped mandrel 20 is engaged with housing 22. One, two, or more sealed fluid channels 100 may be included in microflow assembly 10.

Figure 13D:
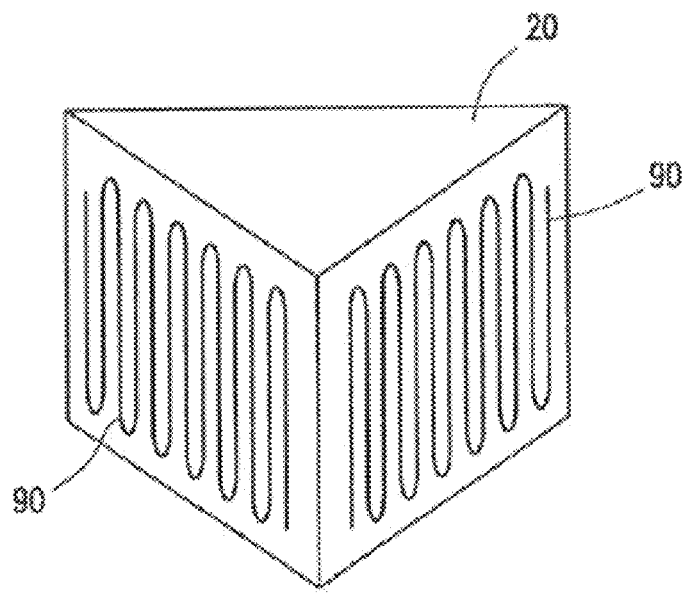
FIG. 13D is a perspective view of a different embodiment of the mandrel.
Figure 13E:
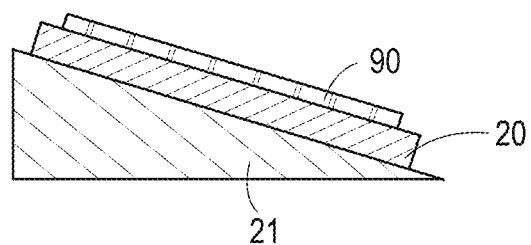
FIG. 13E is a cross-sectional view of another embodiment of the mandrel.

Sealed fluid channel 100 may encircle mandrel 20 or be positioned on a single side of mandrel 20. FIGS. 13A-13D depict mandrels 20 having at least one planar surface upon which protrusion 90 is formed. Protrusion 90 of FIG. 13A forms two sealed fluid channels 100 which move the fluid back and forth across a single surface of mandrel 20. The embodiment in FIGS. 13B and 13C positions protrusion 90 on a single surface of mandrel 20, however sealed channel 100 is formed as a spiral, the fluid exiting the spiral through aperture 71 and channel 72. FIG. 13D depicts mandrel 20 as a wedge, having protrusion 90 positioned on two surfaces of mandrel 20. In some embodiments and as shown in FIG. 13E, protrusion 90 may be positioned upon mandrel 20 having a rectangular cross-section. Wedge 21 may be utilized to move mandrel 20 into the proper position within housing 22.

Protrusion 90 may be configured specifically for the particular surface upon which it is positioned. For example, protrusion 90 which, as shown in FIG. 8, extends along interior surface 86 of cavity 80, may extend beyond the length of mandrel 20 when mandrel 20 is positioned within housing 22.

It is desirable that the height of protrusions 90 are preferably uniform.

In some embodiments, the angles of interior surface 86 of housing 22 and exterior surface 66 of mandrel 20 should be selected so that their uppermost portions present a similarly tapered conical form which enabled mandrel 20 and housing 22 to become self-locking. To achieve this, the taper angle should be essentially at or slightly below the self-clinching angle for the particular material that is being utilized to form protrusions 90 on mandrel 20 and housing 22. For example, polycarbonate materials have a self-clinching angle that is approximately 15 degrees (a 30 degree included angle). Utilizing such a self-locking feature permits a wider range of bonding processes to be successfully utilized on microflow assembly 10.

Figure 14:
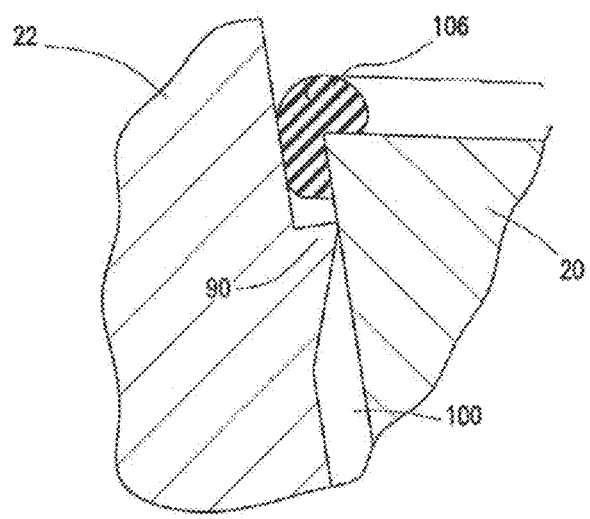
FIG. 14 is a partial cross-sectional view of the mandrel and housing.

Referring to FIG. 14, fluid within cavity 80 passes beyond protrusion 90 and into sealed fluid channel 100. The configuration of mandrel 20 and housing 22 creates a rectangular entrance to sealed fluid housing 100. Bubbles in the fluid are likely to come into contact with an edge of the rectangular entrance, as illustrated in FIG. 14. The rectangular entrance to sealed fluid channel 100 may create pressure points which assist in breaking bubbles such as bubble 106 contained in the fluid.

The configuration of sealed fluid channel 100 may encourage laminar flow, which may be helpful in maintaining an air/water correlation of flow. Fluid flows through sealed fluid channel 100, exiting proximate to dowel 18. Seal 16 prevents the fluid from exiting housing 22 except through passage 42, which ends at assembly outlet 26. Different configurations of microflow restrictor 10 may also include alternate configurations of post 14, connector 12, and housing 22.

Sealed fluid channel 100 may, in particular embodiments, have a height that is greater than about five (5) microns and less than about five hundred (500) microns and a width that is greater than about fifty (50) microns and less than about six thousand (6000) microns. The height of sealed fluid channel 100 may be adjusted by the distance mandrel 20 is inserted into housing 22. The fluid flow through sealed fluid channel 100 may be selected by manufacturing sealed fluid channel 100 with a specific height H, a specific width W, and a specific length L.

Figure 15:
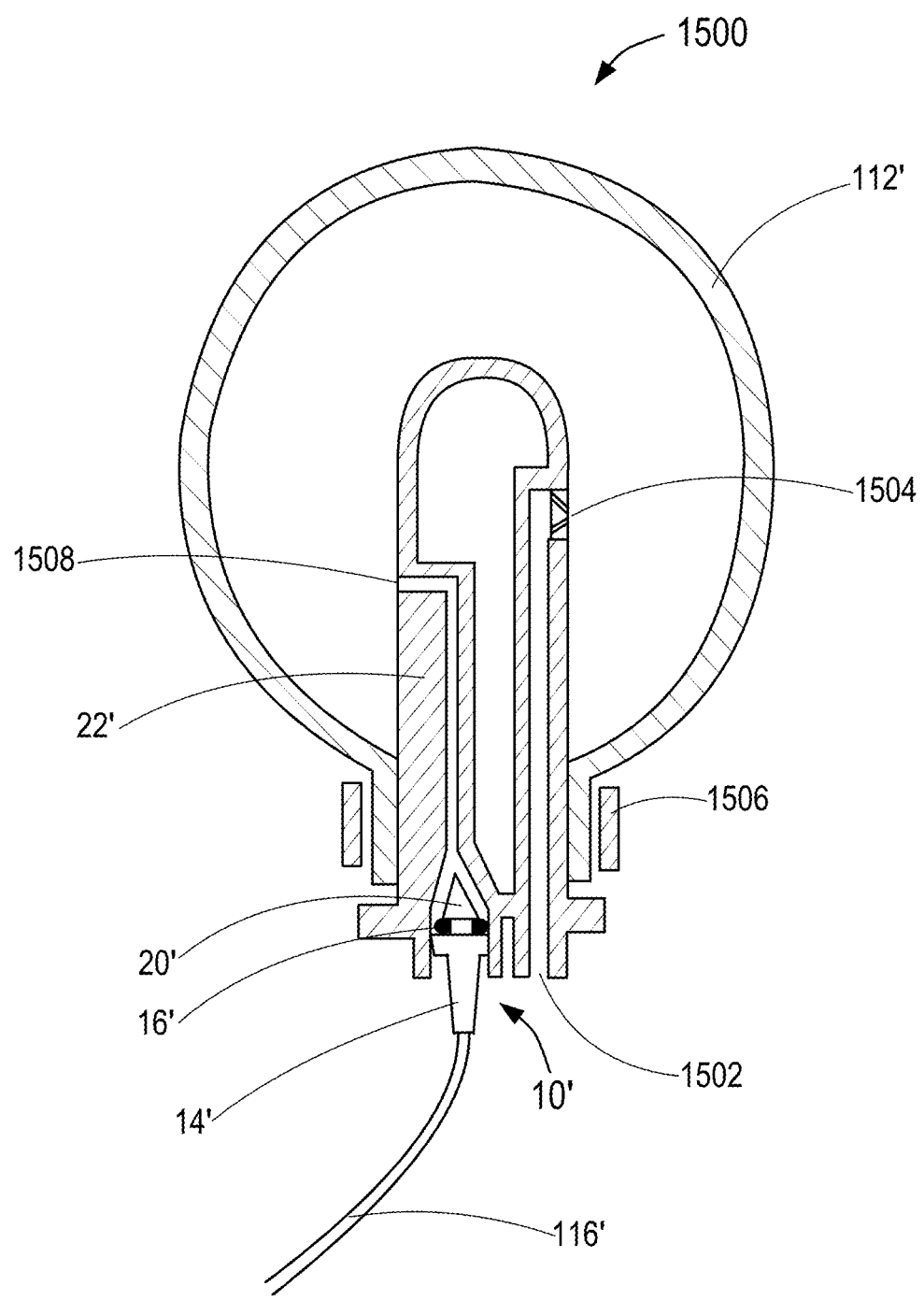
FIG. 15 is a cross-sectional view of an embodiment of the microflow assembly positioned within the reservoir of an ambulatory infusion pump.

Referring to FIG. 15, the microflow restrictor assembly may be formed as an integral component of an ambulatory infusion pump. As shown in FIG. 15, ambulatory infusion pump 1500 may include microflow restrictor assembly 10' incorporated at least partially within reservoir 112'. The components of microflow restrictor assembly 10' may be constructed similar to microflow restrictor assembly 10 of, e.g., FIG. 2A. For example, mandrel 20' of FIG. 15 corresponds with mandrel 20 of FIG. 2A, seal 16' of FIG. 15 corresponds with seal 16 of FIG. 2A, and post 14' of FIG. 15 corresponds with post 14 of FIG. 2A. Post 14' may be positioned within a tube socket. Microflow restrictor assembly 10' includes housing 22', such that mandrel 20', seal 16', and post 14' are positioned within housing 22' to form a sealed fluid channel as described above.

Microflow restrictor assembly 10' may include fill inlet 1502 having a fluid channel extending therethrough from fill inlet 1502 to one-way valve 1504 disposed within reservoir 112'. Reservoir 112' may receive fluid via fill inlet 1502, and one-way valve 1504 may prevent fluid from exiting reservoir 112' through fill inlet 1502. One-way valve 1504 may be any one-way valve known in the art. Microflow restrictor assembly 10' may include inlet 1508 which may permit fluid from reservoir 112' to flow through microflow restrictor assembly 10' and ultimately through medical tubing 116'. In addition, reservoir 112' may be secured on microflow restrictor assembly 10' via ring clamp 1506.

Certain embodiments of microflow restrictor 10 may be assembled in equipment configured to flow air through microflow restrictor 10 from assembly inlet 28 to assembly outlet 26 while a load, either static or impulse, is applied to post 14 which moves mandrel 20 into the appropriate position in housing 22.

Pressure applied to post 14 is used to adjust the rate of fluid flow through microflow assembly 10. Flow rates between 500 ml/hour and 0.5 ml/hour are attainable, and in certain embodiments flow rates between 0.5 ml/hour and 0.01 ml/hour may be attained. As pressure is applied to post 14, the outlet end of post 14 presses on surfaces 60 of bosses 58 which are positioned on dowel 18. Lower surface 54 of dowel 18 moves mandrel 20 further into cavity 80. In selected embodiments, protrusion 90 may be compressed or deformed to reduce the height H of sealed fluid channel 100.

Adjustment of the flow rate and sealing of sealed fluid channel 100 depend on the deformation of protrusion 90 and the surface against which it is deformed. The configuration of apex 96 of protrusion 90 may vary widely, however the smaller area of apex 96 will permit local stresses to form at apex 96 which may exceed the plastic limit of the material from which the protrusion is formed.

To enable the deformation of protrusion 90 positioned on interior surface 86 of housing 22, the material selected to form protrusion 90 may be softer than the material used to form mandrel 20. In contrast, the material used to form mandrel 20 may be selected so that it is softer than the material used to form protrusion 90. In this situation, mandrel 20 will deform around protrusion 90. The same material may be used to form both protrusion 90 and mandrel 20, permitting both to be deformed to form an air-tight seal.

As air flows through microflow assembly 10, the air flow is measured and, in many embodiments of the present invention, the configuration of sealed fluid channel 100 provides for an air/water correlation which will permit accurate calibration of the device. Any potential leaks through seal 16 or other portions of the device will occur after the fluid has passed through sealed fluid channel 100, enabling an accurate flow measurement to be achieved.

An adhesive such as a UV curing adhesive may be applied between post 14 and housing 22 prior to insertion into housing 22 and application of the load to post 14. The desired flow rate through microflow assembly 10 is achieved before the adhesive is cured. The adhesive may also be applied after mandrel 20 has been inserted to the correct position within housing 22 and the desired flow rate achieved, although bumping or other handling may alter the position of post 14 or mandrel 22 and hence the flow rate. Once the adhesive cures, the dimensions of sealed fluid channel 100 are fixed.

Injection molding is an economical and accurate method by which portions of microflow restrictor 10 may be manufactured. During the injection molding process, an injection mold will wear and protrusion 90 may increase in height due to this change. However, the method of assembly accommodates this potential change in the manufacturing process and enables microflow restrictor 10 to be assembled to a pre-set flow rate in the same manner. The method of assembly also accommodates variations in the manufacture of the components.

Figure 16:
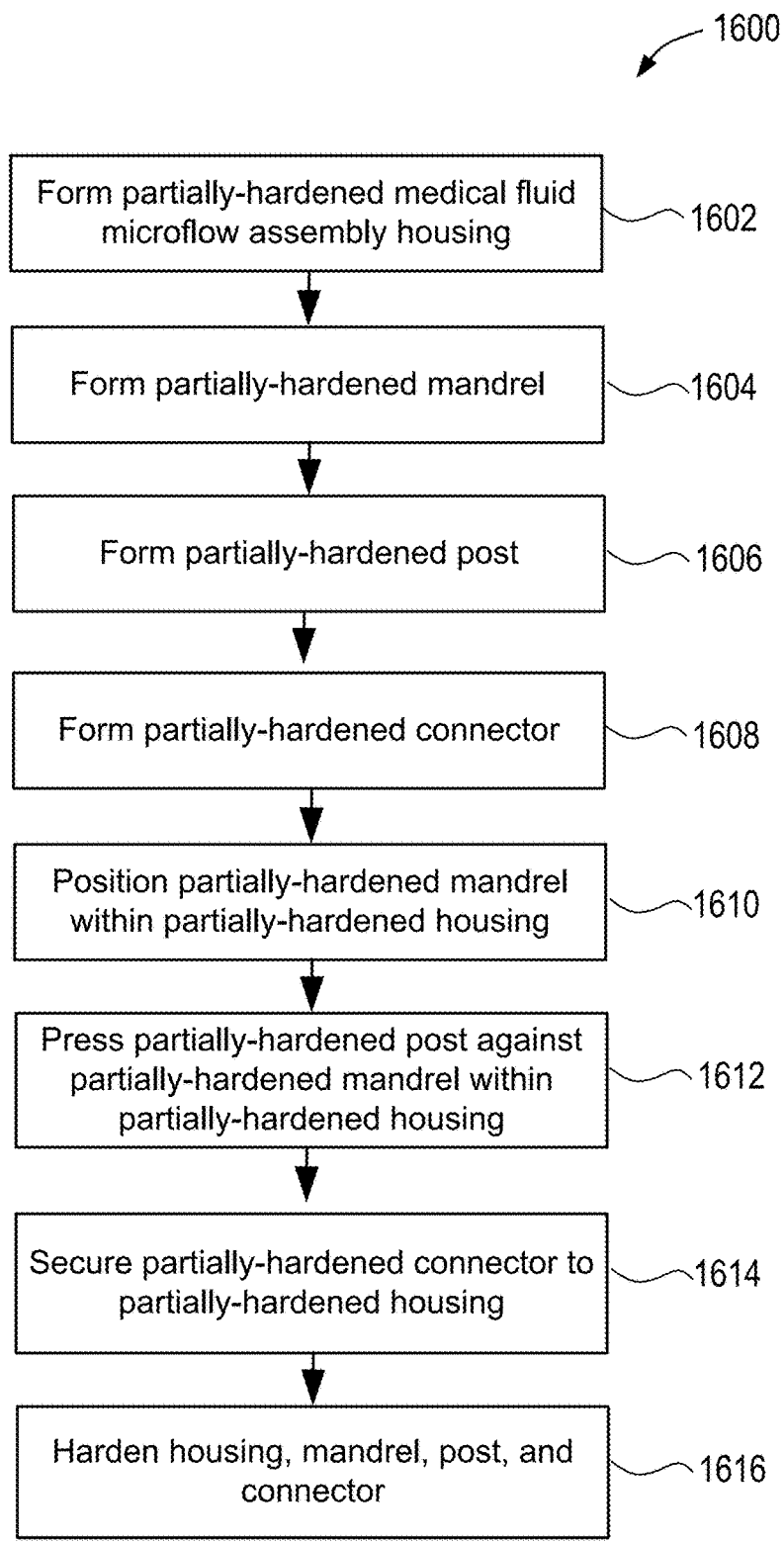
FIG. 16 is a flowchart illustrating an exemplary method of manufacturing a microflow assembly according to an aspect of the present invention.

Referring now to FIG. 16, method 1600 of manufacturing microflow restrictor assembly 10 is described. At step 1602, medical fluid microflow assembly housing 22 having cavity 80 is formed from a material, e.g., plastic, using a machine, e.g., injection molding machine. After injection molding, plastics are uncured in the sense that they are partially-hardened. In the case of polycarbonate, the hardening/curing process takes 3-5 days. Prior to that, the uncured plastic is slightly softer and referred to as "green," e.g., partially-hardened. Other "green" plastics may be used that may be hardened by application of energy, e.g., heat (thermoset), UV, etc. In addition, hardening of the "green" plastic may be prevented or delayed by, e.g., refrigeration, freezing, or a chemical agent. Accordingly, the "green" plastic may subsequently be hardened/cured by reversing the hardening prevention, e.g., by applying heat or another chemical agent.

Similarly, at steps 1604, 1606, and 1608, mandrel 20 having exterior surface 66, post 14 having assembly fluid outlet 26, and connector 12 having opening 34 extending therethrough, are formed from a material, e.g., plastic, using a machine, e.g., injection molding machine. At step 1610, mandrel 20 is positioned within cavity 80 of housing 22 such that at least one partially-hardened uncured protrusion 90 extending from either interior surface 86 of cavity 80 or exterior surface 66 of mandrel 20, as described above, abuts either exterior surface 66 of mandrel 20 or interior surface 86 of cavity 80 to form a sealed fluid channel. The sealed fluid channel includes a channel inlet positioned proximate to fluid inlet 28 and a channel outlet positioned proximate to fluid outlet 26, thereby reducing decrease of flow rate over time within the medical fluid microflow assembly.

The inventors determined, unexpectedly, that using partially-hardened uncured plastic to form protrusion 90 improved consistency in flow rate over time and prevented or minimized the decrease in flow rate over time ("sagging") which may result from micro leaks between the protrusions and the smooth surface of either exterior surface 66 of mandrel 20 or interior surface 86 of housing 22.

The inventors discovered that the slightly lower hardness allows the spiral feature, e.g., protrusion 90, to deform more, and to the point, enough to form an impermeable seal. In one embodiment, protrusion 90 on interior surface 86 of housing 22 is "green," whereas exterior surface 66 of mandrel 20 is hardened plastic. In another embodiment, exterior surface 66 of mandrel 20 is "green," whereas protrusion 90 on interior surface 86 of housing 22 is hardened plastic. In yet another embodiment, both protrusion 90 on exterior surface 66 of mandrel 20 and interior surface 86 of housing 22 are "green". In contrast to the industry standard to wait until plastic cures before assembly, the inventors discovered that assembling components of a medical fluid microflow assembly prior to hardening reduces rate of change of flow rate. For example, the partially-hardened components assembled together may cure to fill in undesirable microgaps between components resulting from the manufacturing process.

Sealing between housing 22 and mandrel 20 is critical to providing consistent flow rates due to the sagging phenomenon described above. Other methods to seal may include, e.g., laser, photon, solvent, vibration, ultrasonic, etc.

At step 1612, post 14 is pressed against mandrel 20 within cavity 80 of housing 22 such that assembly fluid outlet 26 of post 14 is in fluid communication with the channel outlet. At step 1614, connector 12 is secured to housing 22 such that at least a portion of post 14 is positioned within opening 34 of connector 12. As described above, connector 12 may be designed so that connector 12 snaps onto, or is otherwise mechanically connected to, post 14.

In conventional practice, most plastic parts are made in large batches at external vendors and warehoused before assembly, thus providing adequate time for the plastic to harden. However, in accordance with an aspect of the present invention, the uncured components are assembled in a relatively quick time (e.g., less than 12 hours after forming each component, less than 8 hours after forming each component, less than 6 hours after forming each component), thereby reducing sagging. At step 1616, housing 22, mandrel 20, post 14, and connector 12 are hardened/cured. Cure time may be a function of the particular plastic. For example, the cure time/time to harden of PolyCarbonate is 3-5 days, e.g., 36-60 hours.

While steps 1610-1616 describe assembling multiple partially hardened components to form the microflow restrictor assembly, it should be understood that not all components need be partially hardened. For example, in one embodiment, the microflow restrictor assembly is assembled when all components are fully hardened except for housing 22 which is partially-hardened during assembly. In another embodiment, only the mandrel is partially hardened during assembly of the medical fluid microflow assembly. After assembly, housing 22 is allowed to harden/cure, thereby reducing sagging.

Figure 17:
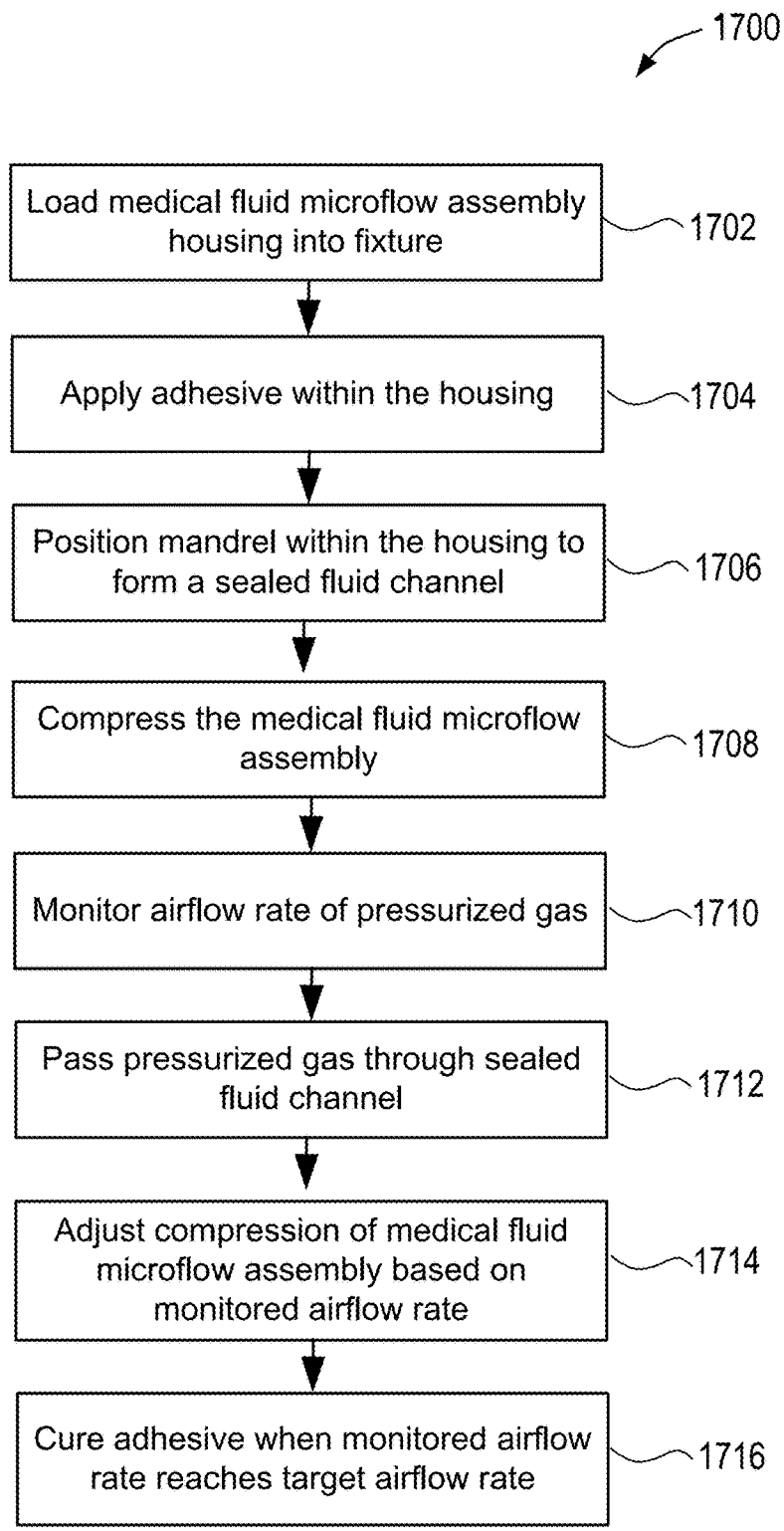
FIG. 17 is a flowchart illustrating an exemplary method of achieving a desired flow rate through the microflow assembly according to an aspect of the present invention.

Referring now to FIG. 17, an exemplary method of achieving a desired flow rate through microflow assembly 10 is described. Method 1700 may be performed using a microflow assembly machine. For example, a microflow assembly machine may include a controller, e.g., computer, a motorized linear actuator, a fixture, a flow meter, e.g., a mass flow meter, and a UV light. At step 1702, microflow restrictor assembly housing 22 is loaded into the fixture of the microflow assembly machine.

At step 1704, a curing adhesive, e.g., UV cure epoxy, is applied on interior surface 86 of housing 22. The adhesive may be applied to a portion of interior surface 86 of housing 22 in the cavity between interior surface 86 and post 14. The adhesive, e.g., Dymax 1160-m-sv01, may include a fluorescing element such that visual or machine vision inspection is easier. In one embodiment, the adhesive may be applied to interior surface 86 of housing 22 before housing 22 is loaded into the fixture. In yet another embodiment, the adhesive may be applied to interior surface 86 of housing 22 after the components of microflow restrictor assembly 10 are cured and microflow restrictor assembly 10 is fixed.

At step 1706, mandrel 20 is positioned within cavity 80 of housing 22 such that at least one partially-hardened protrusion 90 extending from either interior surface 86 of cavity 80 or exterior surface 66 of mandrel 20 abuts either exterior surface 66 of mandrel 20 or interior surface 86 of cavity 80 to form a sealed fluid channel as described above.

At step 1708, post 14 is pressed against mandrel 20 within cavity 80 of housing 22 to compress microflow restrictor assembly 10 by, e.g., the motorized linear actuator or any mechanism well known in the art that may slowly, but consistently increase compression force such as hydraulic or rotary actuators. As described above, using partially-hardened plastic, protrusion 90 may deform more, producing a good seal and preventing sagging.

At step 1710, the airflow rate of pressurized gas, e.g., air or N$_2$, is monitored via the flow meter prior to being passed through the sealed fluid channel at step 1712. In one embodiment, differential pressure across the sealed fluid channel may be monitored via the flow meter. The flow meter provides a near instantaneous value of the air flow rate through the sealed fluid channel. Since the airflow rate correlates with the fluid flow rate, microflow restrictor assembly 10 may be tuned to a desired fluid flow rate by adjusting the compression of microflow restrictor assembly 10 at step 1714 until the airflow rate monitored at step 1708 reaches a target airflow rate.

When the target airflow rate is achieved, and accordingly the desired fluid flow rate through microflow restrictor assembly 10, at step 1716, the adhesive is cured, e.g., by activating the UV light, which cures the adhesive and fixes the location of post 14, and accordingly, the location of mandrel 20 within housing 22. As will be understood by one skilled in the art, the adhesive may be cured by any curing means well known in the art.

Figure 18:
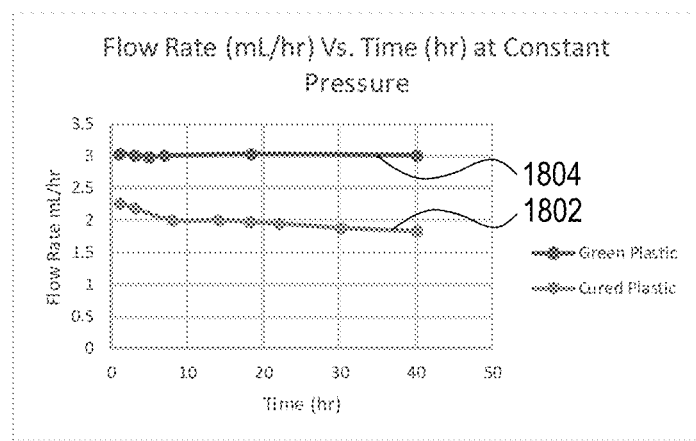
FIG. 18 is a graph illustrating the benefits of manufacturing a microflow assembly with partially-hardened "green" components.

Referring now to FIG. 18, a graph illustrating the benefits of manufacturing microflow assembly 10 with uncured "green" components is described. As described above, using components formed from partially-hardened uncured plastic to manufacture microflow restrictor assembly 10 results in improved consistency in flow rate over time and reduces or even prevents sagging within medical fluid microflow assembly 10. FIG. 18 illustrates the results of an experiment conducted whereby the flow rate of air through a microflow assembly manufactured with hardened plastic components shown by line 1802 was compared with the flow rate of air through a microflow assembly manufactured with uncured "green" plastic components shown by line 1804.

As shown in FIG. 18 and as seen in Table 1 below, the airflow rate through the microflow assembly manufactured with uncured "green" plastic components was consistent over a 40 hour time period (approximately 3 mL/hour). In contrast, as shown in FIG. 18 and as seen in Table 2 below, the airflow rate through the microflow assembly manufactured with hardened plastic components decreased over the 40 hour time period (from 2.27 ml/hour to 1.83 mL/hour).

TABLE 1

Green Plastic Sample

| airflow (sccm) | time (hr) | flow rate (mL/hr) |
|---|---|---|
| 7.16 | 1.00 | 3.045 |
|  | 3.00 | 3.024 |
|  | 4.99 | 2.989 |
|  | 6.98 | 3.006 |
|  | 18.30 | 3.031 |
|  | 40.12 | 3.016 |
|  | % Change: | 0.93 |

TABLE 2

Cured Plastic Sample

| airflow (sccm) | time (hr) | flow rate (mL/hr) |
|---|---|---|
| 7.21 | 1.00 | 2.278 |
|  | 3.00 | 2.193 |
|  | 8.00 | 2.005 |
|  | 14.04 | 2.002 |
|  | 18.08 | 1.977 |
|  | 22.08 | 1.950 |
|  | 30.08 | 1.880 |
|  | 40.08 | 1.832 |
|  | % Change: | 19.59 |

The inventors have discovered, unexpectedly in view of the prior art, that the seizing phenomenon is not due to bubbles and microparticulates, but rather to triboelectric charges created by the fluid flowing through the microflow restrictor. Specifically, the inventors noted that the flow of saline through a restrictor was uninterrupted despite the increased potential for microparticulate clogging while medical grade water for injection exhibited a consistently slower rate of flow over time.

Triboelectric charging is a type of contact electrification in which certain materials come into contact with each other and exchange electrons. This effect is amplified as the fluid and the material of the microflow restrictor assembly are in sliding contact. This causes the materials to become electrically charged. The polarity and strength of the charges that are produced will differ, based on the specific materials and surface roughness of those materials, and the distance between the surfaces. By managing the triboelectric effects of the combined fluid and microflow restrictor, the microflow restrictor is able to consistently function as intended over time.

Managing the triboelectric charge created by a fluid flowing through sealed fluid pathway 100 will necessitate careful consideration of the optimal materials from which mandrel 20 and housing 22 are formed, as well as configuring the surface roughness of each of the surfaces which form sealed fluid channel 100. The materials may be selected to match specific medical fluids. For example, polycarbonate material may be selected for medical saline or glucose solution, including additional medications.

The surface roughness used herein is the average surface roughness $R_a$ which characterizes the surface based on the absolute value of the vertical deviations of the roughness profile from the mean line and is calculated as follows, where y is the height of the deviation from the mean line:

$$R_a = \frac{1}{n}\sum_{i=1}^{n}|y_i|$$

In certain embodiments that are selected for particular applications, interior surface 86 and exterior surface 66 preferably have a surface roughness of between about 0.012 microns and about 5 microns. The surface roughness is desirably less than ten percent (10%), e.g., less than five percent (5%), of the height H of sealed fluid channel 100. While not every surface which forms sealed fluid channel 100 will contact fluid, it is preferred in some embodiments that all surfaces which form sealed fluid channel 100 have a surface roughness which significantly reduces any triboelectric effect from the fluid flowing across the surface. The roughness of surfaces 66 and 86 may also differ from one another.

While many materials may be used to form microflow restrictor assembly 10, including metals and glass, polymers are generally an economical and adaptable material for use. A wide range of polymers is suitable for use in the present invention, and should be selected to correspond to the particular use of the microflow assembly. Polymers such as polycarbonate, polysulfones and acrylic plastics such as poly(methyl methacrylate) (PMMA), PVC (Poly Vinyl Chloride), Nylon, Polyethylene, and polypropylene are useful as materials for forming portions of the microflow restrictor assembly. In particular, medical grade polycarbonate may be used for many potential applications of the microflow assembly. In some embodiments, the polymer selected may be matched to a particular fluid to reduce the triboelectric effects for a particular application of the microflow restrictor assembly. In some embodiments, the material chosen should exhibit a minimal amount of creep.

It should be appreciated by those skilled in the art that various modifications and variations may be made to features of the medical fluid microflow restrictor described herein without departing from the scope and spirit of the invention. It is intended that the invention include all such variations.

What is claimed is:

1. A microflow assembly comprising:
a microflow assembly housing comprising an interior surface;
a mandrel having an exterior surface, the mandrel positioned adjacent to the microflow assembly housing so that at least a portion of the exterior surface of the mandrel is substantially parallel to at least a portion of the interior surface of the microflow assembly housing; and
at least one protrusion extending from either the interior surface of the microflow assembly housing or the exterior surface of the mandrel, the at least one protrusion abutting either the exterior surface of the mandrel or the interior surface of the microflow assembly housing to form an impermeably sealed fluid channel configured to reduce sagging within the microflow assembly, the impermeably sealed fluid channel having a channel inlet and a channel outlet,
wherein the impermeably sealed fluid channel is formed when the at least one protrusion is only partially-hardened, and
wherein at least one of the surfaces which form the impermeably sealed fluid channel has an average surface roughness that is greater than about 0.012 microns and less than about 5 microns.

2. The microflow assembly of claim 1, wherein the impermeably sealed fluid channel has a length and an average width, the length of the channel being greater than ten times the average width of the impermeably sealed fluid channel, the average width of the impermeably sealed fluid channel being at least 50 microns and less than about 6000 microns.

3. The microflow assembly of claim 2, at least a portion of the exterior surface of the mandrel having a conical shape, wherein the impermeably sealed fluid channel extends about the exterior surface of the mandrel in a helical pattern.

4. The microflow assembly of claim 3, wherein the impermeably sealed fluid channel has a constant width along at least a portion of the length of the impermeably sealed fluid channel.

5. The microflow assembly of claim 3, wherein the impermeably sealed fluid channel has a width that varies along at least a portion of the length of the impermeably sealed fluid channel.

6. The microflow assembly of claim 2, the impermeably sealed fluid channel further including an average height which is the average distance between the exterior surface of the mandrel and the interior surface of the microflow assembly housing, wherein the average width of the impermeably sealed fluid channel is at least 3 times the average height of the impermeably sealed fluid channel.

7. The microflow assembly of claim 6, the average height of the impermeably sealed fluid channel being equal to or greater than about five (5) microns and less than about five hundred (500) microns.

8. The microflow assembly of claim 6, wherein at least one of the surfaces which form the impermeably sealed fluid channel have an average surface roughness that is less than about ten percent (10%) of the average height of the impermeably sealed fluid channel.

9. The microflow assembly of claim 1, wherein at least a portion of the exterior surface of the mandrel is planar and at least a portion of the interior surface of microflow assembly housing is substantially parallel to the planar portion of the exterior surface of the mandrel.

10. The microflow assembly of claim 9, wherein the at least one protrusion extends from either the planar portion of the exterior surface of the mandrel or the interior surface of the microflow assembly housing.

11. The microflow assembly of claim 10, wherein at least two portions of the exterior surface of the mandrel are planar, both portions being substantially parallel to the interior surface of the microflow assembly housing, a protrusion being positioned on each planar surface of either the mandrel or the microflow assembly housing so that at least two impermeably sealed fluid channels are formed.

12. The microflow assembly of claim 1, wherein the at least one protrusion further comprises a first surface and a second surface, the first and second surfaces forming an apex which contacts either the exterior surface of the mandrel or the interior surface of the microflow assembly housing to form the impermeably sealed fluid channel.

13. The microflow assembly of claim 12, wherein the apex is formed as a radius that permits local stresses at the apex to exceed a plastic limit of the at least one protrusion.

14. The microflow assembly of claim 1, wherein the impermeably sealed fluid channel is at least partially formed from a material that exhibits a substantially neutral triboelectric charge when in contact with a fluid comprising saline or glucose solution.

15. The microflow assembly of claim 1, wherein the impermeably sealed fluid channel is at least partially formed from polycarbonate.

16. The microflow assembly of claim 1, wherein the impermeably sealed fluid channel is at least partially formed from polycarbonate, polysulfone, acrylic polymers, PVC (Poly Vinyl Chloride), Nylon, Polyethylene, polypropylene, or combinations thereof.

17. The microflow assembly of claim 1, wherein the impermeably sealed fluid channel is configured to permit fluid to flow through the channel outlet at a flow rate greater than about 0.01 ml per hour and less than about 500 ml per hour.

18. The microflow assembly of claim 1, wherein the impermeably sealed fluid channel is configured to permit fluid to flow through the channel outlet at a flow rate greater than 0.01 ml per hour and less than 0.5 ml per hour.

19. A microflow assembly comprising:
a microflow assembly housing comprising an interior surface;
a mandrel having an exterior surface, the mandrel positioned adjacent to the microflow assembly housing so that at least a portion of the exterior surface of the mandrel is substantially parallel to at least a portion of the interior surface of the microflow assembly housing; and
at least one protrusion extending from either the interior surface of the microflow assembly housing or the exterior surface of the mandrel, the at least one protrusion abutting either the exterior surface of the mandrel or the interior surface of the microflow assembly housing to form an impermeably sealed fluid channel configured to reduce sagging within the microflow assembly, the impermeably sealed fluid channel having a channel inlet and a channel outlet,
wherein the impermeably sealed fluid channel is formed by at least one of laser, photon, solvent, vibration, or ultrasonic bonding the at least one protrusion and either the interior surface of the microflow assembly housing or the exterior surface of the mandrel, and
wherein at least one of the surfaces which form the impermeably sealed fluid channel has an average surface roughness that is greater than about 0.012 microns and less than about 5 microns.

20. The microflow assembly of claim 19, wherein at least a portion of the exterior surface of the mandrel comprises a conical shape, and wherein the impermeably sealed fluid channel extends about the exterior surface of the mandrel in a helical pattern.

21. The microflow assembly of claim 19, wherein the impermeably sealed fluid channel has a length and an average width, the length of the channel being greater than ten times the average width of the impermeably sealed fluid channel, the average width of the impermeably sealed fluid channel being at least 50 microns and less than about 6000 microns.

22. The microflow assembly of claim 21, the impermeably sealed fluid channel comprises an average height which is the average distance between the exterior surface of the mandrel and the interior surface of the microflow assembly housing, and wherein the average width of the impermeably sealed fluid channel is at least 3 times the average height of the impermeably sealed fluid channel.

23. The microflow assembly of claim 19, wherein the at least one protrusion further comprises a first surface and a second surface, the first and second surfaces forming an apex which contacts either the exterior surface of the mandrel or the interior surface of the microflow assembly housing to form the impermeably sealed fluid channel.

24. The microflow assembly of claim 23, wherein the apex is formed as a radius that permits local stresses at the apex to exceed a plastic limit of the at least one protrusion.

25. The microflow assembly of claim 19, wherein the impermeably sealed fluid channel is configured to permit fluid to flow through the channel outlet at a flow rate greater than about 0.01 ml per hour and less than about 500 ml per hour.

26. A microflow assembly comprising:
a microflow assembly housing comprising an interior surface;
a mandrel having an exterior surface, at least two portions of the exterior surface of the mandrel being planar, the mandrel positioned adjacent to the microflow assembly housing so that at least a portion of the interior surface of microflow assembly housing is substantially parallel to both planar portions of the exterior surface of the mandrel; and
at least one protrusion extending from each of the planar portions of the exterior surface of the mandrel or the interior surface of the microflow assembly housing, the at least one protrusion abutting either the exterior surface of the mandrel or the interior surface of the microflow assembly housing to form at least two impermeably sealed fluid channels configured to reduce sagging within the microflow assembly, the at least two impermeably sealed fluid channels each having a channel inlet and a channel outlet,
wherein the at least two impermeably sealed fluid channels are formed when the at least one protrusion is only partially-hardened.

* * * * *